United States Patent [19]

Oswald

[11] 4,163,832

[45] Aug. 7, 1979

[54] POLYTHIOETHERS FORMED BY ANIONIC RING OPENING OF EPISULFIDES

[75] Inventor: Alexis A. Oswald, Mountainside, N.J.

[73] Assignee: Exxon Research & Engineering Co., Florham Park, N.J.

[21] Appl. No.: 853,523

[22] Filed: Nov. 21, 1977

Related U.S. Application Data

[63] Continuation-in-part of Ser. No. 618,777, Oct. 2, 1975, which is a continuation of Ser. No. 397,944, Sep. 17, 1973, abandoned, which is a continuation of Ser. No. 23,001, Mar. 26, 1970, abandoned.

[51] Int. Cl.$^2$ ............................................. C08G 18/00
[52] U.S. Cl. ............................... 528/76; 260/609 R; 528/374; 528/376; 528/378; 528/380
[58] Field of Search ............... 260/79, 79.1, 609 R, 260/77.5 AP; 528/374, 378, 380, 76, 376

[56] References Cited

U.S. PATENT DOCUMENTS

| | | | |
|---|---|---|---|
| 2,490,984 | 12/1949 | Snyder | 260/609 |
| 3,320,217 | 5/1960 | Edmonds | 260/79 |
| 3,322,851 | 5/1967 | Berenbaum | 260/830 |
| 3,342,770 | 9/1967 | Osborn et al. | 260/37 |
| 3,373,146 | 3/1968 | Meyer et al. | 260/79.7 |
| 3,403,187 | 9/1968 | Oswald et al. | 260/2.5 AP |
| 3,432,542 | 3/1969 | Ransley | 260/481 |
| 3,448,091 | 6/1969 | Gobran et al. | 260/79 |
| 3,453,126 | 7/1969 | Greco et al. | 260/609 R |
| 3,457,212 | 7/1969 | Fukuoka et al. | 260/31.8 R |
| 3,465,064 | 9/1969 | Signouret | 260/879 |
| 3,466,336 | 9/1969 | Mueller et al. | 260/879 |
| 3,484,418 | 12/1969 | Vandenberg | 260/79 |
| 3,489,728 | 1/1970 | Bailey, Jr. et al. | 260/79 |
| 3,503,940 | 3/1970 | Oswald | 260/79.7 |
| 3,504,050 | 3/1970 | Gobran et al. | 260/823 |
| 3,515,704 | 6/1970 | Woodhams et al. | 260/79 |
| 3,539,676 | 11/1970 | Polestak | 260/79 |
| 3,544,543 | 12/1970 | Greco et al. | 260/609 R |
| 3,567,782 | 3/1971 | Warner et al. | 260/609 |
| 3,579,488 | 5/1971 | Jones et al. | 260/79 R |
| 3,625,925 | 12/1971 | Oswald | 260/37 R |
| 3,644,302 | 2/1972 | Nicco et al. | 260/79 |
| 3,686,326 | 8/1972 | Oswald et al. | 260/836 |
| 4,059,570 | 11/1977 | Oswald et al. | 260/77.5 AP |

FOREIGN PATENT DOCUMENTS

| | | |
|---|---|---|
| 992105 | 6/1976 | Canada . |
| 696774 | 8/1940 | Fed. Rep. of Germany . |
| 1480194 | 4/1967 | France . |
| 1542330 | 9/1968 | France . |
| 6715043 | 5/1968 | Netherlands . |
| 676515 | 3/1968 | South Africa . |
| 445805 | 4/1936 | United Kingdom . |
| 1037982 | 8/1966 | United Kingdom . |
| 1082565 | 9/1967 | United Kingdom . |
| 1147617 | 4/1969 | United Kingdom . |
| 1246316 | 9/1971 | United Kingdom . |
| 1348045 | 3/1974 | United Kingdom . |

OTHER PUBLICATIONS

Wylde, Bulletin de la Societe Chimique de France, 1967, No. 5, pp. 1603–1607.
Oswald, Polymer Preprints, vol. 13, No. 1, Apr. 1972, pp. 57–60.
Adamek et al., Rubber and Plastics Age, Jan. 1965, pp. 56–57, 59, 60 and 62.

*Primary Examiner*—Melvyn I. Marquis
*Attorney, Agent, or Firm*—Albert P. Halluin

[57] ABSTRACT

Episulfides are reacted with mono, di or trithiols in the presence of tertiary aliphatic amines or tertiary aliphatic phosphines, to form corresponding thioether thiols by a highly selective anionic mechanism. Increasing episulfide-thiol ratios result in polythioether thiols of increasing molecular weights. Using two or more episulfides, block copolymers can be prepared. The reactive terminal thiol functionality and the segmented crystalline and amorphous block structure of the new polymers makes them particularly useful for castable rubber applications.

56 Claims, No Drawings

POLYTHIOETHERS FORMED BY ANIONIC RING OPENING OF EPISULFIDES

CROSS REFERENCE TO RELATED APPLICATIONS

This application is a continuation-in-part of U.S. Application Ser. No. 618,777, filed Oct. 2, 1975, which in turn is a continuation of U.S. Application Ser. No. 397,944, filed Sept. 17, 1973, now abandoned, which in turn is a continuation of U.S. Application Ser. No. 23,001, filed Mar. 26, 1970, now abandoned.

BACKGROUND OF THE INVENTION

This invention relates to a selective anionic ring opening process which comprises reacting episulfides with thiols in the presence of tertiary amines. More specifically, this invention relates to polythioether dithiols and polythiols which are derived by reacting episulfides according to the process of this invention with dithiols and polythiols, respectively.

Several anionic ring opening reactions of episulfides are known in the prior art. For example, U.S. Pat. Nos. 2,490,984 and 2,497,100 describe the nonselective anionic ring opening of episulfides by thiols in the presence of sodium thiolates as catalysts, e.g.

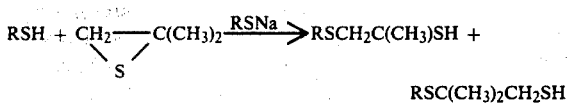

wherein R is an alkyl group.

The anionic ring opening of episulfides by primary and secondary amines is also known. The reaction was reviewed in some detail by M. Sander (see *Chemical Reviews*, 66, 331-333, (1966)). For example, A. Oddon and J. Wylde reported that secondary amines selectively open the propylene episulfide ring via an anionic mechanism to form the corresponding secondary aminoethanethiols; e.g.,

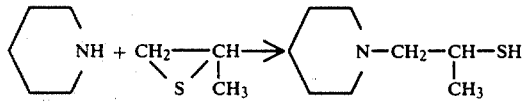

(For reference see *Bull Soc. Chim.*, France, pp. 1603-1607, 1967).

The ring opening of episulfides by thiols in the absence of catalysts is known (see German Pat. No. 696,774). However, such reactions require higher temperatures.

It is believed that the present tertiary aliphatic amine catalyzed ring opening of episulfides by thiols is most closely related to a similar ring opening of epoxides. In contrast to the products of this invention, the epoxide ring opening products are, however, generally discolored as a result of the formation of colored by-products.

Many polythioethers derived from episulfides by anionic ring opening reaction are also known. P. Sigwalt in a review article (P. Sigwalt, "Ring Opening Polymerization", 2, 191-217 (1969) in a series of monographs on "Kinetics and Mechanisms of Polymerization", Ed. K. C. Frisch, M. Dekker, New York, N.Y.) discusses the various catalysts, among them sodium thiolates and tertiary amines, which have been used to effect anionic episulfide polymerizations. (For reference also see *Chimie Industrie-Genie Chimique*, 96, 909, (1966) and S. Adamek, B. B. J. Wood and R. T. Woodhams, *Rubber and Plastics Age*, 56 (1965)).

Anionic ring opening reactions of episulfides with compounds of metals of Group Ia of the Mendeleef Periodic Table in the presence of a compound containing a labile hydrogen atom as a chain transfer agent are known to the art; see for example, South African Application No. 65/1838.

In recent years a number of patents covering various sulfur containing polymeric compositions have issued, e.g., U.S. Pat. Nos. 3,403,187; 3,432,542; 3,465,064; 3,466,336; 3,484,418; 3,503,940; 3,504,050; 3,544,543; 3,625,925; 3,644,302 and 3,686,326. These patents do not, however, teach, suggest or disclose polythioether thiol compositions having the stereoregular feature, i.e., units of the same orientation relative to the thiol group.

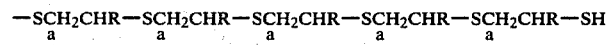

These patents do not teach that certain tertiary amine and tertiary phosphine catalysts will selectively cause a ring opening of the episulfide in the presence of thiols to obtain the aforementioned stereoregular polythioether thiols.

British Patent Specification No. 1,082,565 to Cameron discloses a process for preparing "Flexibiliser C" wherein hydrogen sulfide is reacted with propylene sulfide in the presence of N-benzyldimethylamine at 60° C. Cameron states at page 2, lines 62-74:

"The aforesaid flexibilisers, many of which are known compounds, may readily be obtained from the monoepisulfide and the compound containing at least two hydrogen atoms as aforesaid by reaction in the presence of an acid catalyst, such as boron trifluoride diethyl etherate, or a basic catalyst such as sodium ethoxide or N-benzyldimethylamine. If the compound used to react with the monoepisulfide is an amine, addition of a catalyst is usually unnecessary." Among the compounds containing at least two hydrogen atoms attached directly to nitrogen or sulfur which may be used to form the flexibilizing agents include hydrogen sulfide and polythiols. The Cameron specification does not teach the combination of using more than one episulfide or the importance of selecting certain tertiary amines or phosphines for preparing polymers having stereoregularity.

Copolymers of two or more episulfides are also known to be formed by anionic reactions, as it is disclosed in U.S. Pat. No. 3,317,920. Most of such copolymers were prepared to incorporate minor amounts of olefinic episulfides whose double bond could be subsequently utilized for the crosslinking of the resulting polythioethers by conventional sulfur vulcanization methods. In all these preparations the copolymerization of various episulfides occurred in a statistically random fashion.

SUMMARY OF THE INVENTION

It has surprisingly been found that thioetherthiols may be prepared via the amine or phosphine catalyzed ring opening of episulfides by thiols. Where the thiol is a polythiol, the reaction products are polyfunctional polythioetherthiols.

The monothioetherthiols of the invention are useful as intermediates for the synthesis of pesticides. The polythioether dithiols and polythiols are suitable for use as mastics and rubbers.

The preferred episulfides are ethylene episulfide and propylene episulfide. Where the episulfide is an unsymmetrical episulfide, e.g. propylene episulfide, the resultant product is the thiol isomer which is more highly substituted at the alpha-carbon atom. (Reference is made to U.S. Application Ser. No. 32,457, filed Apr. 27, 1970, now U.S. Pat. No. 4,101,557, issued July 18, 1978, for a process for preparing the episulfides.)

DETAILED DESCRIPTION OF THE INVENTION

This invention relates to a selective anionic ring opening process which comprises reacting episulfides with thiols in the presence of tertiary amines and phosphines. More specifically, this invention relates to a process for preparing polyfunctional polythioetherthiols which are suitable as mastics and rubbers and may be readily crosslinked by conventional techniques.

In accordance with this invention, episulfides are reacted with thiol compounds, the reaction being catalyzed by amine or phosphine base catalysts to form thioether thiols and amine or phosphine complexes thereof.

Among the episulfides suitable for use in the practice of this invention are those episulfides having the general formula:

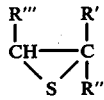

wherein R', R" and R'" are hydrogen, hydrocarbyl radicals and substituted hydrocarbyl radicals. In a preferred embodiment R" and R'" are hydrogen, $C_1$–$C_{30}$ hydrocarbyl radicals or $C_1$–$C_{30}$ substituted hydrocarbyl radicals; preferably R" and R'" are $C_1$–$C_6$ alkyl, $C_5$–$C_8$ cycloalkyl, phenyl or tolyl; more preferably R" and R'" are hydrogen, methyl or ethyl; most preferably R" and R'" are both hydrogen. R' as defined above preferably comprises $C_1$ to about $C_{200,000}$ radicals; more preferably a $C_1$ to $C_{30}$ radical; most preferably R' is a $C_1$–$C_{16}$ hydrocarbyl radical; e.g. $C_1$–$C_4$ alkyl, allyl or propargyl. For example, R' may be ethyl or methyl.

The term $C_1$ to $C_{30}$ hydrocarbyl radical includes acyclic, alicyclic or aromatic and the acyclic or alicyclic radicals may be either saturated, unsaturated, linear or branch chained radicals. The alicyclic radicals may be single ring, bridged or fused ring compounds.

Illustrative examples of these $C_1$ to $C_{30}$ hydrocarbyl radicals are methyl, propyl, isopropyl, secondary amyl, tertiary amyl, isooctyl, dodecyl, hexadecyl, docosyl, tetracosyl, triacontyl, vinyl, propenyl, hexenyl, cyclobutyl, cyclopentyl, cyclohexyl, norbornyl, tetrahydroindyl, alkyl substituted derivatives of these alicyclic compounds, phenyl, naphthyl, anthranyl, aralkyl, alkylaryl, etc.

The substituents of the R' hydrocarbyl radical can be hydroxy, hydrocarbyloxy, hydrocarbylthio, carbohydrocarbyloxy, acyl, alkylene sulfide or alkylene oxide groups. When used in the specification and claims, the term "substituted hydrocarbyl radical" means the hydrocarbyl radicals disclosed herein substituted with one or more of the aforementioned substituents. Preferably, the substituted hydrocarbyl radicals contain oxygen and/or sulfur. The oxygen or sulfur may exist as ether or carbonyl groups and thioether or thioketone groups respectively. Both oxygen and sulfur in either or both forms may be present in the same radical. In principle, however, any substituent can be present which does not enter into undesirable side reactions with the thiol or base catalyst component. The term "substituted hydrocarbyl radical" includes hydrocarbyl radicals substituted by a hydrocarbylene polyether group. Such a hydrocarbylene polyether group can be a polyalkylene oxide, a polyalkylene sulfide, a polyalkylene polysulfide. Similarly, R' can be a polyester substituted hydrocarbyl radical.

The term "unsymmetrical episulfide" means an episulfide wherein R', R" and R'" are not the same. The term "monosubstituted episulfide" means an episulfide wherein at least two of the groups R', R" or R'" are hydrogen and the other is as previously defined but not hydrogen.

Illustrative of the episulfides suitable for use in the practice of this invention are ethylene sulfide, propylene sulfide, butadiene monosulfide, dodecene sulfide, dotriacontene sulfide, cyclohexene sulfide, styrene sulfide, stilbene sulfide, polybutadiene sulfide, 3-hydroxypropylene sulfide, 3-allyloxypropylene sulfide, 3-phenylthiopropylene sulfide, 3-dichlorophenoxythiopropylene sulfide, 3-acetylthiopropylene sulfide, 3-diethoxythiophosphorylthio-propylene sulfide, isopropylidene-bis-p-phenoxypropylene sulfide, bis-3-thiopropylene sulfide, 1,5-hexadiene sulfide, diallyl polytrimethylenethioether sulfide, N-phthalimidopropylene sulfide, etc. Preferred of these are ethylene sulfide and propylene sulfide.

The thiol reactants suitable for use in the practice of this invention are represented by the general formula:

wherein R is hydrogen or an organic radical, preferably R is an organic radical of about $C_1$ to $C_{200,000}$ carbon atoms, more preferably, R is a hydrocarbyl radical or substituted hydrocarbyl radical; and m is an integer representing the valence of R, preferably m varies from about 1 to 500, more preferably from about 1 to about 50, most preferably m is about 1 to about 10, e.g. 1 to 4.

In a preferred embodiment, R is a hydrocarbon or substituted aliphatic hydrocarbon radical, more preferably a substituted aliphatic radical. The substituents on the radical can be oxy, thioethers, esters, halogenated aromatic groups, dialkyl amino groups, etc. Both oxygen and sulfur may be present in the same radical. The oxygen or sulfur may exist as ether or carbonyl groups and thioether or thioketone groups, respectively. For example, R can be a polyalkylene thioether radical wherein the hydrocarbon chain is interrupted by sulfur atoms. The aliphatic radical can be a primary, secondary or tertiary radical. In an embodiment of this invention, R is an organic radical containing about 1 to about 1,000 carbons, preferably, it is a $C_1$ to $C_{100}$ radical, more preferably a $C_1$-$C_{30}$ radical; most preferably R is a hydrocarbon radical of about 1 to about 30 carbon atoms and more preferably 2 to 12 carbon atoms. Ideally R is an aliphatic hydrocarbon radical of about 1 to about 10 carbon atoms; preferably about 1 to 6 carbon atoms and m is less than 4, e.g. 3. It will be obvious to those skilled in the art where R is H, m must be 1 and the thiol reactant is $H_2S$. Where m is 1 and R is an organic radical, the reactant is a monothiol. Where m is 2 or 3, the thiol is di- or tri-thiol, respectively.

Aliphatic polythiols, e.g. dithiols are the preferred polythiols of this invention. Illustrative examples of the thiols suitable for use in the practice of this invention are:

Monothiols: methanethiol, n-butanethiol, i-propanethiol, t-dodecanethiol, dotriacontane thiol, polyethylene thiol, hydroxyethanethiol, carboethoxymethanethiol, 5-hexenethiol, cyclopentanethiol, cyanoethanethiol, chlorobenzenethiol, dinitrobenzenethiol, 2-benzothiazolethiol, alpha-toluenethiol, polyethylenesulfidethiol, t-butylthioethanethiol. Dithiols: ethanedithio, 1,3-propanedithiol, 1,4-butanedithiol, hexamethylene dithiol, dotriacontanedithiol, cyclohexanedithiol, benzene-dithiol, xylylenedithiol, polymethylenedithiol, polypropylene-sulfidedithiol, ethylenebis-oxyethanethiol, diphenylsulfide-dithiol, bis-methylenecarboalkoxyethanethiol, 3-hydroxypropanedithiol. Polythiols: propanetrithiol, benzenetrithiol, beta,beta, beta-triethylcyclohexanetrithiol, cyclododecanetrithiol, polybutadienepolythiol, polypropylenesulfide polythiol, octanetrithiol, deodecanetetrathiol, hexadecanepentathiol, tri-mercaptopropionyltriazin, tetra-mercaptoethyl silane, tri-mercaptopropyl phosphate, trimethylol propane trimercaptopropionate, tri-mercaptopropyl carbinol, polyethylenemaleate polythiol, pentaarythritol tetramercaptoproprionate.

The term "organic thiols" as used in the specification and claims means the monothiols, dithiols and polythiols of this invention.

The synthesis of the starting hydrocarbon trithiols and polythiols is often expensive. A preferred method of trithiol and polythiol synthesis uses the addition of excess hydrogen sulfide to a triolefin or polyolefin. The resulting polythioether polythiols can be used as advantageous starting materials for the present syntheses. Similarly the polythiol adducts of hydrogen sulfide to triacryloyl triazine, triacryloyl ester, triallylcarbinol, etc., can be used.

The reaction of thiols with the episulfides of this invention is represented by the general equation:

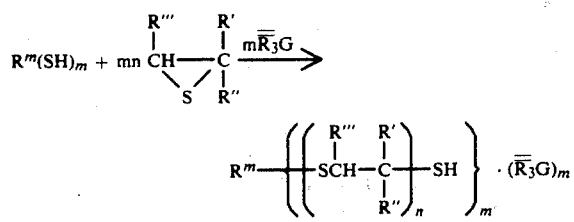

wherein R, R', R", R'" are as previously defined, $\bar{R}$ is hydrogen, a $C_1$ to $C_{30}$ hydrocarbyl radical, $C_1$-$C_{30}$ substituted hydrocarbyl radical, G is nitrogen or phosphorus, and m and n are integers of 1 or greater. $\bar{R}$ is preferably a $C_1$ to $C_6$ alkyl group. In carrying out the reaction, it is not essential that the catalyst and thiol be present in equimolar quantities based on this thiol functionality.

Where R" and R'" of the episulfide are hydrogen, the reaction is represented by the equation:

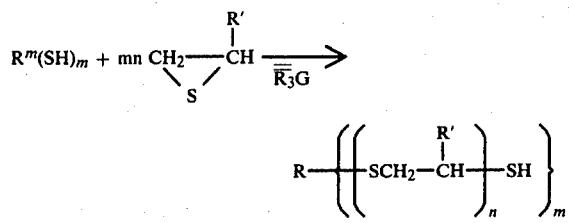

where the thiol compound is $H_2S$, the reaction may be represented as follows:

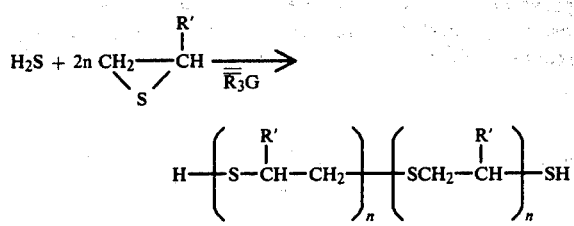

Similarly, the reaction of mono, di and trithiols with the episulfides of this invention is represented by the equation:

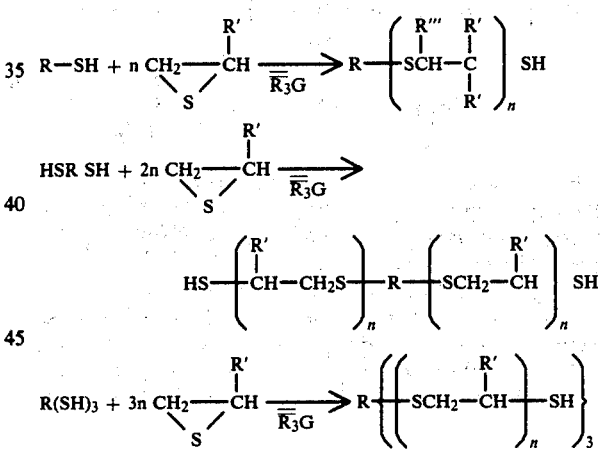

It will be obvious to those skilled in the art that a mixture of various episulfides may be coreacted with the thiol compound. The polythioether polythiol products of the present invention can be further reacted with an episulfide different from the one used in their preparation.

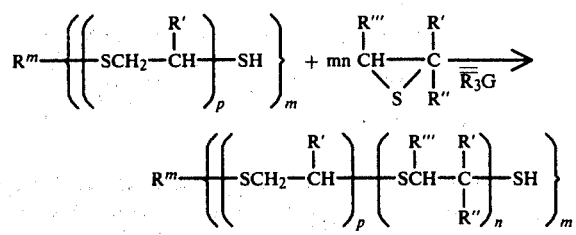

wherein the meaning of the previously used symbols is the same and p is a number of about 0 to 20,000, preferably 1 to about 1,000.

The same type of sequential reaction can be carried out using a mixture of ethylene episulfide and a less reactive substituted derivative.

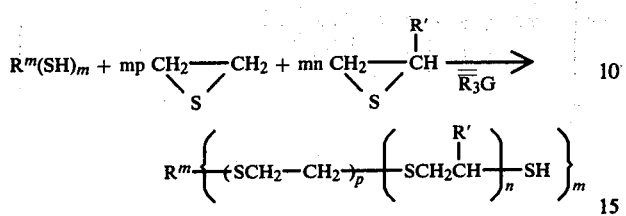

After the original episulfide mixture reacts, a new mixture can be added to form further blocks of the polymer. This procedure can be repeated at will. The resulting transformations are shown by the following reaction scheme.

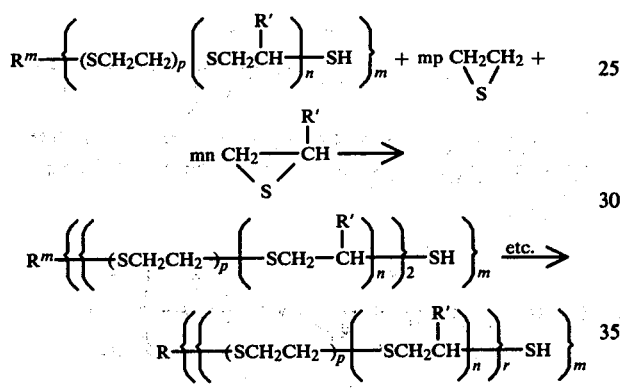

wherein r is an integer equivalent to the number of times the step is repeated; preferably r is less than 10. A particularly advantageous feature of the present process is the possibility of stepwise reactions to form linear polymers having both amorphous aliphatic regions and crystalline regions. For example, these block polymers may be prepared by reacting dithiols with ethylene episulfide and then further reaction of the product with propylene episulfide. The reaction is described by the following equation:

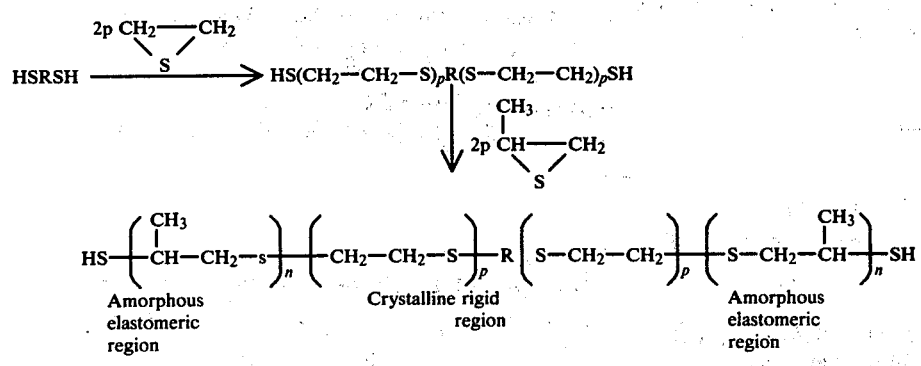

Due to the higher reactivity of ethylene episulfide in the presence of the present selective amine catalysts essentially the same product can be prepared by using a mixture of ethylene and propylene sulfide. The reactants will react in the same sequence as shown by the above scheme.

Instead of propylene episulfide, other alkyl substituted ethylene sulfides of increased reactivity can be also used for the preparation of similar block copolymers.

Although the episulfides of this invention have been generally described as linear or branched chain episulfides, compounds having cyclic constituents may be used. These compounds have the general formula:

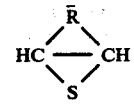

wherein $\bar{R}$ is a $C_2$-$C_{10}$ alkylene or $C_2$-$C_{10}$ alkenyl radical. For example, illustrations of compounds wherein $\bar{R}$ is $C_4$ are:

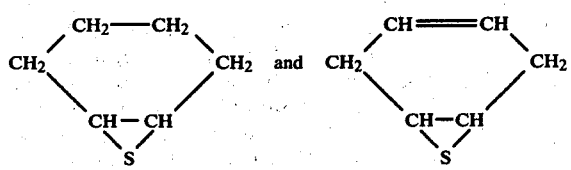

Polyfunctional episulfides may also be used in the practice of this invention. These compounds of course react to form highly crosslinked networks, e.g.

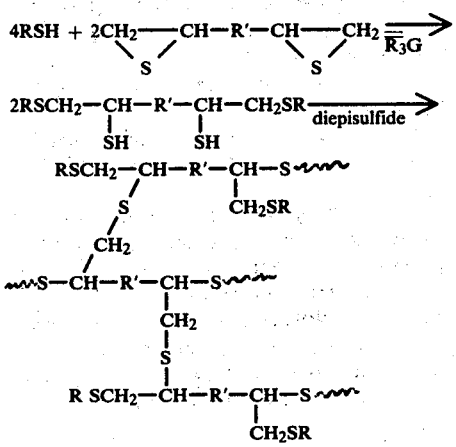

crosslinked network

R' may be a divalent hydrocarbyl or substituted hydrocarbyl radical of about 1 to 20 carbon atoms. Preferably, R' is a $C_2$ to $C_8$ alkylene radical.

Polymeric compositions such as polybutadiene may be modified to have pendant of the backbone episulfide groups. These polymers may be crosslinked by reaction with polythiols. A preferred polythiol is prepared by reacting polybutadiene with $H_2S$ in the presence of a free radical catalyst. The reaction is preferably carried out in an excess of $H_2S$.

The reactions of this invention are carried out in the presence of a tertiary organoamine or tertiary organophosphine catalyst. The tertiary amines or phosphines can be cyclic compounds containing one or more nitrogen or phosphorus atoms. For example, tertiary heterocyclic nitrogen compounds such as pyridine or triethylene diamine may be used.

The amine catalysts of this invention may be represented by the schematic formula $N\bar{\bar{R}}_s$ wherein s is an integer of 1, 2 or 3 and $\bar{\bar{R}}$ is advantageously selected from the group consisting of hydrogen, $C_1$ to $C_{30}$ hydrocarbyl radicals and $C_1$ to $C_{30}$ substituted hydrocarbyl radicals; preferably $C_1$ to $C_{12}$ hydrocarbyl radicals; more preferably $C_1$ to $C_6$ hydrocarbyl radicals; most preferably, $\bar{\bar{R}}$ is a $C_1$ to $C_{12}$ aliphatic hydrocarbyl radical, more preferably a $C_1$ to $C_6$ aliphatic hydrocarbyl radical; $\bar{\bar{R}}$ can be $C_1$ to $C_{10}$ alkyl, $C_4$ to $C_{10}$ alicyclic hydrocarbyl radicals or mixtures thereof, e.g. cycloalkylene or cycloalkylidene. It will be evident that where s is less than 3, at least one $\bar{\bar{R}}$ is a cyclic radical. For example, where s is 2, the compound may be N-ethyl piperidine; where s is 1, the compound may be pyridine. The cyclic amines may be alkyl substituted in one or more positions, said alkyl groups containing about 1 to about 6 carbon atoms. Illustrative examples of the $\bar{\bar{R}}$ radical are methyl, propyl, hexyl, amyl, octyl, isooctyl, dodecyl, cyclohexylene, cyclohexylidene, etc.

It will be evident to those skilled in the art that where s is 1, the compound is heterogeneous cyclic compound such as pyridine; where s is 2, the compound is a cyclic compound such as N-ethyl-piperidine; where s is 3, the compound is a triorgano amine. Preferably, s is 3 and $\bar{\bar{R}}$ is a $C_1$ to $C_6$ hydrocarbyl radical; more preferably $\bar{\bar{R}}$ is a $C_1$ to $C_6$ alkyl or alkenyl radical; most preferably $\bar{\bar{R}}$ is methyl, ethyl, propyl or butyl.

Where the amine or phosphine is a triorgano compound, it may be represented by the general formula $\bar{\bar{R}}_3 G$ wherein $\bar{\bar{R}}$ is advantageously selected from the group consisting of $C_1$ to $C_{30}$ hydrocarbyl radicals and $C_1$ to $C_{30}$ substituted hydrocarbyl radicals and G is N or P. Preferably, $\bar{\bar{R}}$ is $C_1$-$C_{30}$ aliphatic radical, most preferably, $\bar{\bar{R}}$ is a $C_1$-$C_{18}$ alkyl radical. $\bar{\bar{R}}$ may also be a $C_4$-$C_8$ cycloalkyl group. Preferably G is N.

The triorgano amine catalysts of this invention may be represented by the schematic formula $N\bar{\bar{R}}_3$ where $\bar{\bar{R}}$ is as earlier defined and s is an integer of 1 to 3.

The metal free tertiary alkylamine catalysts of the present invention have several advantages above those described in the prior art. They can be, in general, readily removed by distillation after the ring opening reaction is complete. Also in many cases these same amines can be used to advantage again as catalysts in subsequent chain extension and crosslinking reactions of polythioetherpolythiol products. Furthermore, their use allows a better control of the molecular weights of the products. In fact, polymers of the molecular weights corresponding to the thiol episulfide ratio can be produced at will using tertiary alkylamine catalysts.

Illustrative of the amine catalyst of this invention are trialkyl amines such as trimethylamine, hexadecyldimethylamine, didodecylmethylamine, quinuclidine, methylethylhexylamine, tri-i-propylamine, triethanolamine, triallylamine, tripropargylamine, dimethylbenzylamine, N-methyl piperidine, N-methylmorpholine; bis-amines such as N,N'-dimethylpiperazine, tetramethylethylenediamine, triethylenediamine; hexamethylene tetramine, alpha,alpha'-dimethyldotriacontylamine, pentamethyldiethylentriamine, pyridine, quinoline, N-methyl imidazole, N-ethyl piperidine, pyrazine, quinoxaline, thiazole; dimethyl amine; diisopropyl amine, ethyl hexyl amine, methyl dodecyl amine, diethanol amine morpholine; primary amines such as ethyl amine, hexyl amine, dodecyl amine, docosylamine, tricontyl amine, ethanol amine, hydroxypropyl amine, ethyl aminopropionate, amino acetone.

The preferred amine catalysts useful in the practice of the present invention include trimethylamine, tetramethylazabicyclooctane, N,N,N',N'-tetramethylethylenediamine, triethylenediamine and trans-2,5-dimethylpiperazine. Trimethylamine is the most preferred amine catalyst on the basis of its high basicity, lack of steric crowding and low cost. These preferred amines are capable of catalyzing the ring opening of the episulfide in the presence of the thiol of hydrogen sulfide reactant to obtain the compositions of the invention at low temperatures, i.e., temperatures of about 40° C. and lower (although the reaction will proceed at higher temperatures, it is not desirable to utilize the higher temperatures due to increased cost and reduced selectivity).

It is shown in Examples 13, 16 and 17 that other amines such as pyridine, dimethylaniline and triethylamine are not comparable catalyst for the ring opening reaction between the episulfide and thiols at room temperature. In addition, it can be shown that dimethylbenzylamine (as disclosed in British Pat. No. 1,082,565) does not catalyze the ring opening of episulfides in the presence of trimethylenedithiol at room temperature, but apparently will catalyze the ring opening at 60° C. in the presence of hydrogen sulfide.

Illustrative examples of the tertiary organophosphines of this invention are trimethyl phosphine, tributyl phosphine, tridecyl phosphine, diethylhexyl phosphine, P-ethylphosphetane, triallyl phosphine, dimethylcyclohexyl phosphine, tetramethyl ethylene diphosphine.

In contrast to most of the prior art methods, the present novel ring opening of episulfides by thiols in the presence of trialkylamines is highly selective. When starting with unsymmetrical episulfides, such as propylene sulfide, the method produces the thiol isomer which is more highly substituted at the alpha-carbon atom:

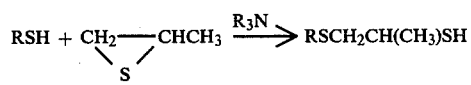

The present selective ring opening process is highly advantageous for the production of novel polythioesters having secondary thiol end groups. By using several episulfides in the process, polythioether block copolymers having crystalline and elastomeric segments are prepared. By substituting polythiols for monothiols, polythioether polythiols are derived. The reactive terminal functionality of the latter is advantageous for castable rubber applications and the like.

The amine catalyst forms a hydrogen bonded complex with thiol compounds. Such complexes can be in equilibrium with the corresponding ammonium thiolate salts. The polarization of the complex seems sufficient to significantly increase the nucleophilicity of the thiol sulfur for attacking the episulfide ring at the less substituted carbon. Not wishing to be bound by theory, it is thought that the reactions of this invention proceed as indicated by the following scheme with mono thiols and monosubstituted episulfides.

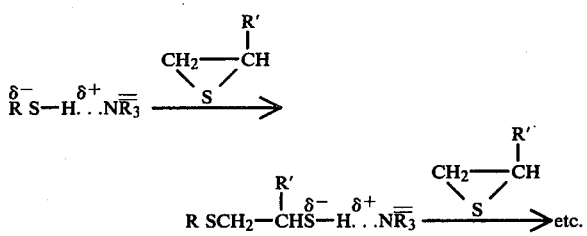

The greater the polarization of the complex, the higher is the anionic reactivity of the thiol in the ring opening of the episulfide. Further reaction takes place with additional amounts of episulfide to form polythioetherthiols:

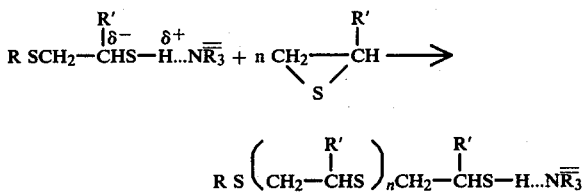

The polymerization of the thiol in the catalyst complex is dependent on both the thio and the catalyst. The higher the thiol's acidity, the greater is the anionic character of the complex. Due to their greater anionic character, amine complexes of aromatic thiols show higher reactivities than those of the aliphatic thiols. The basicity of the catalyst is also directly related to the reactivity of the complex; therefore, aliphatic amines are preferred to the aromatic amines. Bicyclic aliphatic amines with an exposed unshared electron pair on the nitrogen such as triethylenediamine are particularly effective catalysts because of the reduced steric crowding.

The effectiveness of the catalyst will be, of course, also dependent on the episulfide reactant. Ethylene episulfide, for example, shows a much higher reactivity than propylene episulfide.

The ratio of tertiary amine catalyst to thiol is not critical. In general, higher ratios result in greater reaction rates. Amine catalysts can be used in quantities ranging from about 0.01 moles or more per mole of thiol reactant; preferably, about 0.01 to about 2 moles per mole of thiol reactant; more preferably 0.05 to about 1.5 moles; most preferably about 0.1 to about 1 mole.

The ratio of episulfide to thiol reactants will determine the molecular weight of the product. The lesser amount of thiol reactant used, the higher the molecular weight of the resultant product. The episulfide reactant to thiol ratio is not critical. It can be as little as 0.005; preferably about 0.005 to about 10,000; more preferably, about 1 to 2000; most preferably from 0.5 to 1000. For the preparation of monothioetherthiols from episulfide-monothiol reactions, reactant ratios of about 0.5 to 2 are preferred. For the synthesis of polythioether thoils, thiol compounds, i.e., di- or polythiols, are reacted with approximately the number of episulfide molecules per thiol one desires to link up by ring opening into a macromolecule.

The reactions of this invention can be carried out at any convenient temperature. The preferred range is about $-100°$ C. to $+150°$ C. The higher temperatures favor the ring opening of the episulfide; however, they reduce the hydrogen bonding between the thiol and the amine and therefore diminish the activity of the amine catalyst. Consequently, the lower temperatures are preferred in the practice of this invention. More preferably, the reaction is carried out at 0° to 120° C., most preferably 20° to 70° C., e.g., 25° to 40° C. As mentioned above, the preferred amines catalyze the reaction at temperatures below 40° C., preferably from 0° to 40° C. and more preferably from 15° to 30° C.

The pressure at which the reaction is carried out is not critical; however, it should be sufficient to maintain all of the reactants in the liquid phase at the elevated temperatures. Superatmospheric pressures may be necessary. The preferred pressure range is about 1 atmosphere to 50 atmospheres, more preferably about 1 atmosphere to 10 atmospheres.

Although solvents are not necessary for the reactions since the episulfides themselves are liquids, solvents may be used to control the reaction temperature and in the case of solid products, maintain the reaction system in a homogeneous liquid state. Any solvent which is a solvent for the episulfides and the products and does not react with the amine or episulfides is suitable. An excess of tertiary amine may be used as a solvent. However, the preferred solvents are aromatic hydrocarbons, thioesters, chlorinated aromatic hydrocarbons, N,N-dialkylamides and esters. The ethylene episulfides and propylene episulfides may be used in excess as solvents also.

Illustrative examples of the solvents which may be used in the practice of this invention are toluene, diethyl sulfide, chlorobenzene, dimethyl formamide, ethyl acetate, diethyl sulfone, thiophene, ethanol, etc.

Solvents in which some reactants and/or products are insoluble can be advantageously used to make the higher molecular weight polythioether products of this invention, for example, by emulsion polymerization. Suitable media for such systems include water, methanol, cyclohexane, tetrahydrofuran, methyl ethyl ketone, etc.

The present novel process provided new compositions, i.e., secondary and tertiary thioether dithiols, trithiols and polythiols of the general formula:

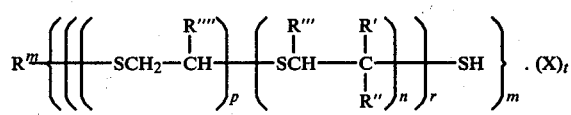

R, m and r are as previously defined; X is the amine or phosphine catalyst of this invention; R" and R"' are hydrogen, $C_1$ to $C_{30}$ nonsubstituted and substituted hydrocarbon radicals, preferably alkyl radicals, most preferably hydrogen, methyl, ethyl. If R" is hydrogen, R"' must also be a hydrogen. R"" is selected from the group consisting of hydrogen and $C_1$ to $C_4$ aliphatic hydrocarbon radicals such as alkyl, allyl, propargyl; more preferably, R'''' is hydrogen or methyl. Most preferably, R'''' is hydrogen. R' is selected from the group consisting of substituted and nonsubstituted monovalent hydrocarbon radicals in the $C_1$ to $C_{200,000}$ preferably in the $C_1$ to $C_{30}$ range. More preferably, R' is a $C_1$ to $C_{16}$ open chain aliphatic hydrocarbyl radical, especially a $C_1$ to $C_4$ alkyl, allyl or propargyl radical. The symbol n is an integer of 1 to 50,000, preferably 2 to 20,000, more preferably 2 to 3000, most preferably 3 to about 1000; p represents a number of 0 to 20,000, more preferably 0 to about 3000, most preferably 1 to 1000. r is 1 to 10, preferably 2-3 and more preferably 1. t is 0 or a number of about 0.01 to about 10, preferably 0 to 3. Where t is 0, the uncomplexed thiol terminated thioether is introduced. Where t is an integer, the compound is the thiol complexed with the catalyst. Since the thiol may be a polythiol and the catalyst may be used in quantities less than equimolar with respect to the thiol, t need not be an integer. Preferably t is about 0 to 5; more preferably t is 0.

The term "thioether thiol compound" as used in the specification and claims means both the uncomplexed thiol and the thiol complexed with the catalyst of this invention.

In a more specific embodiment such compositions include those of the general formula

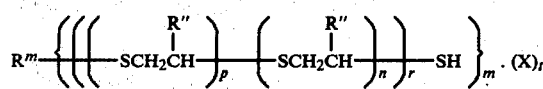

wherein the meaning of symbols is as previously defined.

More specifically such compositions include those of the formula

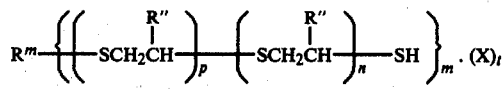

wherein the meaning of symbols is the same.

Most specifically such compositions include those having the formula

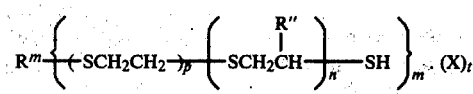

wherein the symbols have the meaning specified before.

In other specific embodiments such compositions include those of the formula

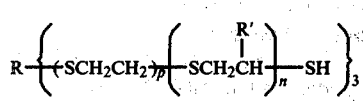

wherein the symbols have the same meaning as specified earlier. $R^2$ and $R^3$ represent di- and trivalent radicals respectively.

In another specific embodiment, the new compositions include those of the general formula

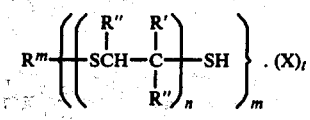

wherein the symbols are as previously defined except n is 2 to 50,000, preferably 3 to 20,000, more preferably 3 to 3000, most preferably 3 to 1000.

This embodiment also includes compositions of the formula

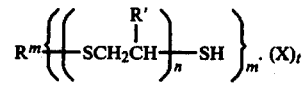

wherein the meaning of the symbols is as indicated above.

More specific compositions of this embodiment are the following:

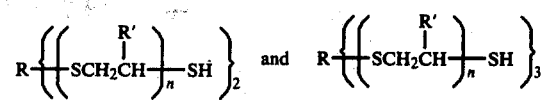

The new compositions include those of the general formula

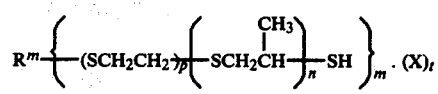

wherein the meaning of $R^m$ and $(X)_t$ is as previously defined; m is 2 to 50, preferably 1 to 10, more preferably 3; n is 2 to 50,000, preferably 2 to 20,000, more preferably 2 to 3000, most preferably 3 to 1000; p is 0 to 20,000, preferably 0 to 20,000, more preferably 0 to 3000, most preferably 1 to 10,000.

These compositions include compounds of the formula

and

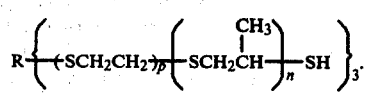

The following polypropylenesulfide-secondary thiol compositions having specific structures are within the scope of this application:

specifically

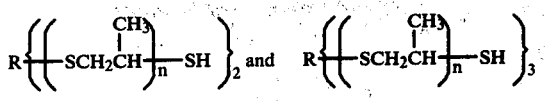

The hydrogen sulfide-episulfide oligomer compositions of the invention include those of the generl formula

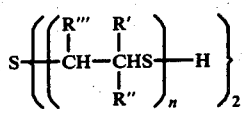

more specifically

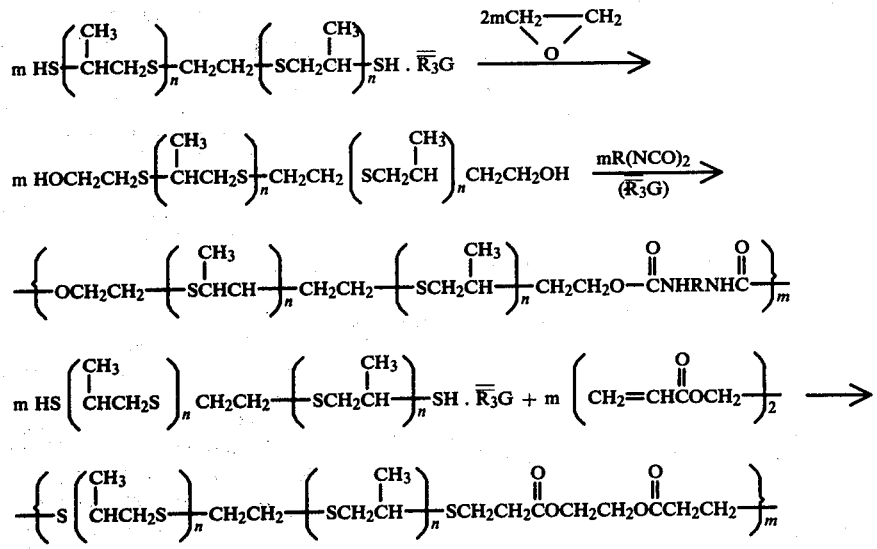

most specifically

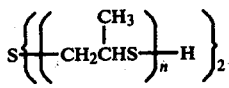

wherein n is 1 to 50,000, preferably 1 to 20,000 more preferably 1 to 3000, most preferably 1 to 1000.

The polythioether thiol products of the present invention are useful polymers in the field of elastomers, coatings, adhesives and plastics applications. The secondary or tertiary rather than primary nature of the thiol groups of the present compositions is importnt in these applications. It results in a slower crosslinking, longer shelf life. The less reactive character of the novel compositions also allows their use as initiators for the free radical polymerization of vinylic monomers such as styrene.

Although the novel polythioether dithiols and polythiols are less reactive, they can be chain extended and/or crosslinked with known reagents for thiol groups to produce useful compositions. Suitable reagents include peroxides such as lead peroxide, epoxides such as diepoxides, polyunsaturates such as triacrylates, etc. The desirable degree of crosslinking, of course, is dependent on the intended field of application. A low degree of crosslinking results in highly elastomeric products, while highly crosslinked compositions behave as tough plastics.

The low molecular weight thioether thiol compositions are useful as polymer additives and pesticides and intermediates for the same.

In several of the chain extension and crosslinking reactions, it is advantageous to use the amine complexes of the present polythioether dithiols and polythiols as produced. The reaction of the thiol groups with epoxides, isocyanates, acrylates, maleates is catalyzed by amines. The same amines used in the present episulfide ring opening reaction of thiols are effective for the subsequent chain extension and crosslinking reactions. The reaction conditions are also the same. As illustrative examples, for the chain extension of the present polythioether dithiols the following reaction schemes are given:

For other reactions, such as oxidation by peroxides, the amine is best neutralized or/and removed.

Since the catalyst polymer complexes are unstable at elevated temperatures, e.g., above 120° C., the polymer may be readily recovered by stripping off the catalyst at temperatures of about 20° to about 150° C., preferably at about 50 to about 120° C. It is preferred that the stripping operation be carried out at reduced pressures, preferably about 1 to about 500, more preferably about 10 to about 200.

Alternately, the catalyst may be removed by mild acidification of the polymer-catalyst complex followed by extraction, e.g. with water. Suitable acids which may be used are carbon dioxide, carboxylic acids such as acetic acid, inorganic acids such as HCl, H₂SO₄, BF₃. Preferably, the acid is used in stoichiometric amounts based on the catalyst or in the case of weak acids it can be also used in an excess of about 1 to about 50% above the amount equivalent to the amine catalyst, more preferably about 5 to about 10% excess.

In general, the vulcanization of the free polythioether polythiols can be accomplished by the methods used for polysulfide polymers. For a detailed description of these methods see *High Polymers,* Vol. XII, part III, edited by N. Gaylord and published by the Interscience Division of J. Wiley & Sons (1962) incorporated herein by reference.

As can be observed from the above description of the invention, the following preferred compositions are included within the scope of the invention:

I. Polythioether thiol compounds having the general formula

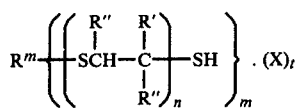

wherein R is a $C_1$ to $C_{200,000}$ hydrocarbyl radical or a $C_1$ to $C_{200,000}$ hydrocarbyl radical substituted with oxyethers, thioethers, esters, halogenated aromatic groups, and dialkylamino groups; R' is a $C_1$ to $C_{200,000}$ hydrocarbyl or $C_1$ to $C_{200,000}$ hydrocarbyl radical substituted with hydroxy, hydrocarbyloxy, hydrocarbylthio, carbylhydrocarbyloxy, acyl, alkylene sulfide and alkylene oxide groups; R" and R''' are hydrogen or $C_1$ to $C_{30}$ hydrocarbyl radicals, with the proviso that if R" is hydrogen, R''' is also hydrogen; X is a tertiary organoamine or tertiary organophosphine; n is an integer of 2 to about 50,000; m is an integer of 1 to about 10; and t is an integer of 0 to 3. Preferably R has a maximum of 1000 carbon atoms; R' is a $C_1$ to $C_4$ hydrocarbyl radical, R" and R''' are hydrogen; n is an integer of 2 to about 3,000; and m is an integer of 1 to 4. X is preferably an organoamine and most preferably trimethylamine. R' is most preferably methyl. The value of m can be 1 to 10, but preferably is a value of 1, 2 or 3, etc., and most preferably 1 or 3 and higher, e.g., up to 10. These thiol compositions may be vulcanized to become useful industrial products. The block copolymers as described below are especially preferred compounds of the invention.

II. Secondary or tertiary polythioether thiol block copolymers having the general formula

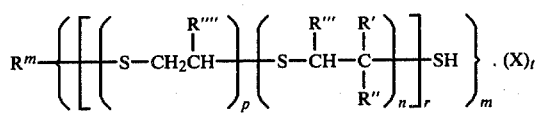

wherein R is a $C_1$ to $C_{200,000}$ hydrocarbon radical or a $C_1$ to $C_{200,000}$ hydrocarbon radical substituted with oxyethers, thioethers, esters, halogenated aromatic groups, dialkylamino groups; R' is a $C_1$ to $C_{200,000}$ hydrocarbyl or $C_1$ to $C_{200,000}$ hydrocarbyl radical substituted with hydroxy, hydrocarbyloxy, hydrocarbylthio, carbohydrocarbyloxy, acyl, alkylene sulfide and alkylene oxide groups; R" and R''' are each independently selected from the group consisting of hydrogen, $C_1$ to $C_{30}$ hydrocarbyl radicals with the proviso that if R" is hydrogen, R''' must also be hydrogen; R'''' is selected from the group consisting of hydrogen and $C_1$ to $C_4$ aliphatic hydrocarbyl radical; p is an integer of 1 to about 1,000; n is an integer of 1 to about 50,000; r is an integer of 1 to about 10; m is an integer of 1 to about 500; X is a tertiary organoamine or a tertiary organophosphine; and t is an integer of 0–10. Preferably, R has a maximum of 1000 carbon atoms; m is an integer of about 1 to about 10, R' is a $C_1$ to $C_4$ hydrocarbon radical; R" and R''' are hydrogen and t is an integer of 0-3. More preferably, R is a $C_1$ to $C_{30}$ aliphatic hydrocarbon radical; R' is a $C_1$ to $C_4$ hydrocarbyl radical selected from the group consisting of alkyl, allyl, and propargyl; R", R''' and R'''' are hydrogen; m is an integer of 2 or 3; p is an integer of 1 to about 1000; n is an integer of about 2 to about 3,000; r is an integer of 2 to 3; and t is an integer of 0 to 3. Especially preferred block copolymers are those of the above general formula (II) wherein R is a $C_2$ to $C_{12}$ hydrocarbyl radical; R' is methyl; R", R''' and R'''' are hydrogen; X is trimethylamine; m is an integer of 2 or 3; n is an integer of about 1 to about 20,000; p is an integer of about 1 to about 1000 and t is an integer of 0 to 3.

Another preferred group of block copolymers of the invention are represented by the following general formula:

III. Secondary polythioether polythiol block copolymers having the general formula

wherein R is a $C_1$ to $C_{1000}$ hydrocarbon radical or a $C_1$ to $C_{1000}$ hydrocarbon radical substituted with oxyethers, thioethers or esters; R' is selected from the group consisting of a $C_1$ to $C_{30}$ hydrocarbon radical, a $C_1$ to $C_{30}$ hydrocarbyl radical substituted with hydroxy, hydrocarbyloxy, hydrocarbylthiol, carbohydrocarbyloxy, acyl, alkylene sulfide, and alkylene oxide groups; R'''' is hydrogen or $C_1$ to $C_4$ aliphatic hydrocarbyl radical; m is an integer of 1 to about 50; n is an integer of 1 to about 50,000; p is an integer of 1 to about 1,000; r is an integer of 1 to about 10; X is a tertiary organoammine; and t is an integer of 0 to 3. Preferably, R'''' is hydrogen and p is 1.

Still another preferred specific group of block copolymers of the invention are represented by the following general formula:

IV. Secondary polythioether dithiol block copolymers of the formula

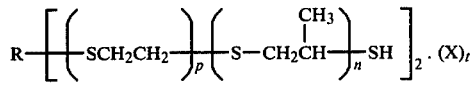

wherein R is a $C_1$ to $C_{200,000}$ divalent hydrocarbon radical or a $C_1$ to $C_{200,000}$ hydrocarbon radical substituted with oxyethers, thioethers, esters, halogenated aromatic groups, dialkylamino groups; p is an integer of 1 to about 1000; n is an integer of 1 to about 50,000; X is trimethylamine and t is an integer of 0 to 3. Preferably R is a divalent $C_1$-$C_{30}$ hydrocarbon radical and more preferably R is a divalent aliphatic hydrocarbon radical having 1 to 6 carbon atoms and t is 0. The symbol n is preferably an integer of about 2 to about 3000.

The block copolymers represented by the general formulae II, III and IV may also be vulcanized to useful industrial products.

The advantages of the process and the resulting compositions of this invention may be more readily appreciated by reference to the following examples. It is noted that in these examples the CH3 group is abbreviated as Me for the sake of brevity.

Reactions of Monothiols with Propylene Episulfide

EXAMPLE 1

To a mixture of 37 g. (0.5 M) propylene episulfide and 3.0 g. (0.05 M) trimethyl amine in a Pyrex pressure tube equipped with a magnetic stirrer and a Teflon pressure valve, was condensed 27 g. (0.56 M) of methanethiol at −80° C. The resulting reaction mixture was sealed and then mixed while cold. Then the tube was placed into an 18° C. constant temperature water bath and the contents stirred there for 72 hours to complete the reaction.

The reaction may be illustrated by the following equation:

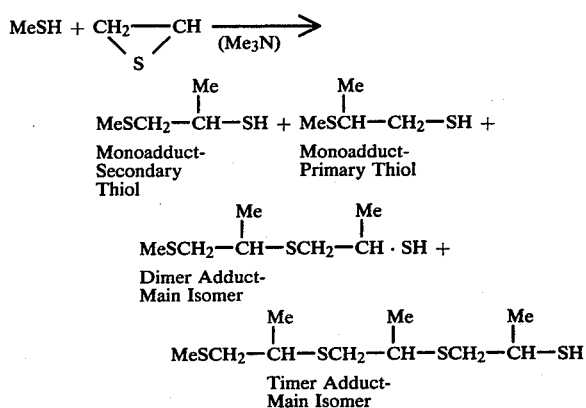

The progress of the reaction was followed by the examination of the composition of samples, periodically taken from the reaction mixture, by nuclear magnetic resonance spectroscopy. Nmr has indicated that about 75% of the episulfide reacted in 6 hours. There was no unreacted episulfide in the reaction mixture after 72 hours.

The crude reaction product was fractionally distilled in vacuo. At first 21 g. colorless liquid monoadduct, distilling at 73°-74° C. at 10 mm, was obtained. As the second product, the diadduct, 14 g. of a colorless liquid distillate, boiling at 79°-80° C. at 0.05 mm was received. About 11 g. of the product remained as a colorless liquid distillation residue. Nmr indicated that about 82% of this residue, i.e. about 9 g. was the triadduct. The above product distribution indicated that about 29% of the episulfide was converted to the monoadduct. About 31 and 17% of the epoxide was used in the formation of the di- and tri-adduct, respectively.

The calculated composition of the monoadduct fraction, $C_4H_{10}S_2$, is the following: C, 39.30; H, 8.24; S, 52.46. Found: C, 39.56; H, 8.37; S, 52.40. Nmr and gas-liquid partition chromatography (glc) of this fraction show that at least 97% of the monoadduct has the secondary thiol structure.

The calculated composition of the diadduct is $C_7H_{16}S_3$, i.e. C, 42.81; H, 8.21; S, 48.98. Found: C, 42.73; H, 8.83; S, 49.20. Nmr and glc analyses showed that essentially all the diadduct had the secondary thiol structure.

Similarly the triadduct was shown by nmr to be the secondary thiol isomer.

EXAMPLE 2

To 18.5 g. (0.25 M) propylene episulfide in a Pyrex pressure tube, 1.43 g. (0.025 M) allylamine and then 12 g. (0.25 M) methanethiol were added at −80°. The contents were then sealed and mixed at −30°. The reaction mixture was allowed to warm to room temperature and to stand for 72 hours with stirring. On subsequent workup by fractional distillation in vacuo most of the starting episulfide was recovered unreacted. Between 73°-74° at 20 mm, 1.2 g. of a liquid distillate product was obtained. Nmr showed that this product was a 3 to 2 molar mixture of the 1-methylthio-2-propanethiol described in the previous example and of 1-allylamino-2-propanethiol formed by the following side reaction:

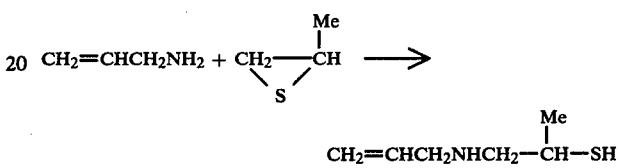

The liquid distillation residue, 0.7 g., was apparently a mixture of oligomeric adduct derivatives of the same compounds.

EXAMPLE 3

To 1.9 g. (0.05 M) of trimethyl phosphine in a Pyrex tube, 20.0 g. (0.42 M) methanethiol and then 18.8 g. propylene sulfide were condensed at about −70°. The closed contents were mixed and then allowed to come to 12°. After being stirred for 72 hours at that temperature to complete the reaction, the unreacted components were removed under 30 mm pressure by film evaporation. The yellow liquid residual product weighed 26 g. and according to nmr, consisted mainly of the expected monoadduct product of Example 1, i.e. 1-methylthio-2-propanethiol.

On fractional distillation of the crude product, 1 g. of crystalline trimethylphosphine sulfide byproduct was isolated. During the distillation some decomposition and a darkening of the residual mixture were observed.

EXAMPLE 4

To a mixture of 55 g. (0.5 M) benzenethiol and 37 g. (0.5 M) propylene episulfide, 3 g. (0.05 M) of trimethylamine catalyst was added. The reaction mixture was then stirred in a constant temperature bath at 15° C. for 24 hours. Nmr analyses indicated that about 80% of the episulfide has reacted in 6 hours. In 24 hours the reaction was complete.

The reaction may be described by the following equation:

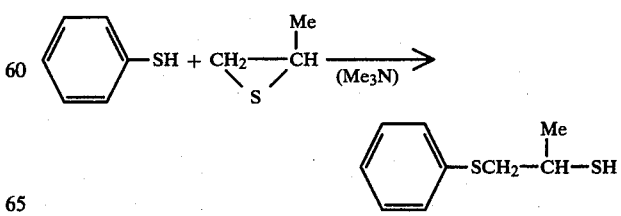

Nmr showed that the crude product consisted essentially of the above secondary thiol monoadduct, i.e.

1-phenylthio-2-propanethiol. Fractional distillation of the crude product in vacuo yielded 87 g. (94.5%) of purified monoadduct as a colorless distillate boiling at 69°–70° for 0.05 mm. Glc indicated 99% purity for the distilled product.

Analyses calculated for $C_9H_{12}S_2$: C, 58.65; H, 6.56; S, 34.79. Found: C, 58.17; H, 6.47; S, 35.17.

The distillation residue (4 g.) consisted primarily of the diadduct according to nmr.

EXAMPLE 5

To a mixture of 35.8 g. (0.2 m) 3,4-dichlorobenzenethiol and 14.9 g. (0.2 M) propylene episulfide was condensed 1.2 g. (0.02 M) trimethylamine catalyst at 0° C. This resulted in the formation of small amounts of a solid thiol-amine complex. Stirring of the heterogeneous reaction mixture for 5 hours at 15° C. resulted in an essentially complete reaction to form the monoadduct, i.e. 3,4-dichlorophenylthio-2-propanethiol, as indicated by nmr. The reaction may be represented by the following equation:

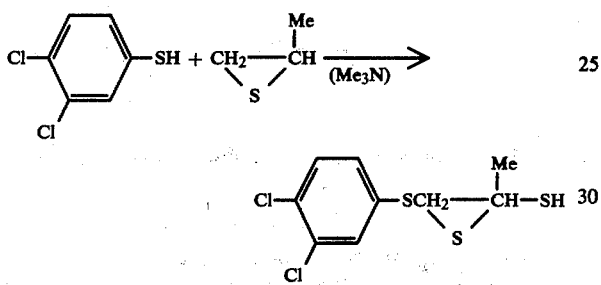

The reaction mixture was allowed to stand at room temperature for two days. Then it was purified by fractionation in vacuo to yield 47 g. (93%) of the secondary thiol monoadduct as a colorless liquid boiling between 95°–96° C. at 0.01 mm.

Analyses calculated for $C_9H_{10}Cl_2S_2$: C, 42.69; H, 3.98; S, 25.33. Found: C, 43.23; H, 4.17; S, 25.36.

Other substituted aromatic thiols, such as 4-cyanobenzenethiol, 4-nitrobenzenethiol, 4-methylthiobenzenethiol, are reacted with propylene episulfide in a similar manner to provide the corresponding substituted 1-phenylthio-2-propanethiols.

EXAMPLE 6

Propylene episulfide is reacted with ethanethiol in the manner described in Example 1 to yield 1-ethylthio-2-propanethiol as the major product.

Substituted aliphatic thiols, such as 3-chloropropanethiol, 3-hydroxypropanethiol, 3-cyanopropanethiol are reacted with propylene episulfide in a similar manner to provide the corresponding substituted 1-propylthio-2-propanethiols.

Reactions of Monothiols with Other Episulfides

EXAMPLE 7

To a mixture of 60 g. (1 M) ethylene episulfide and 96 g. (2 M) methanethiol in a pressure tube, 0.75 g. (0.012 M) trimethylamine was condensed in liquid nitrogen. The closed tube was then placed into a dry ice-alcohol mixture to melt the reactants and then to mix them by shaking. After removal from the bath, the homogeneous mixture was then allowed to come to room temperature while being magnetically stirred. Within 15 minutes, an exothermic reaction occurred which resulted in the precipitation of a yellowish, white solid. The mixture was quickly cooled in dry ice-alcohol and then stirred at room temperature for 18 hours.

The occurring ring opening reaction may be illustrated by the following scheme:

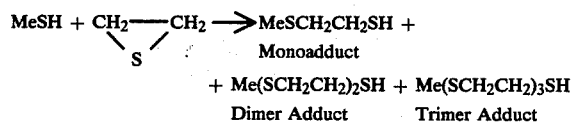

The unreacted methanethiol was then released and the mixture diluted with 300 ml. methanol. The mixture was then filtered with suction. The methanolic filtrate was distilled. After the removal of the solvent, 15.3 g. of the monoadduct was obtained as a colorless, mobile liquid distillate between 48°–49° at 0.1 mm. The second vacuum distillate fraction consisted of 16.8 g. of dimer adduct boiling at 68°–70° under 0.1 mm pressure.

The waxy solid precipitate product was stirred with 200 ml. toluene. The toluene filtrate was then evaporated and the residue purged with nitrogen at 150° under 0.15 mm pressure. The residual product solidified at room temperature. It was 19.6 g. and consisted mostly of the trimer adduct.

A calculation indicated that 14% of the starting episulfide was used for the formation of the monoadduct. The dimer adduct and the trimer adduct had incorporated 20% and 30% of the original episulfide, respectively.

The structure of the mono-, di- and triadduct fractions was indicated by the relative intensities of their methyl and ethylene proton signals in their nmr spectra. The structures were supported by elemental analyses.

Analyses calculated for the monoadduct, $C_3H_8S_2$: C, 33.29; H, 7.45; S, 59.26. Found: C, 33.43; H, 7.41; S, 59.41—Calculated for the dimer adduct, $C_5H_{12}S_3$: C, 35.67; H, 7.18; S, 57.15. Found: C, 35.92; H, 7.36; S, 56.92—Calculated for the trimer adduct $C_7H_{16}S_4$: C, 36.80; H, 7.06; S, 56.14. Found: C, 37.29; H, 6.88; S, 56.23.

EXAMPLE 8

About 0.85 g. (0.015 M) of trimethylamine was reacted with 35.8 g. (0.2 M) dichlorobenzenethiol resulting in the formation of a solution of the solid thiol-amine complex in the excess thiol. About 12 g. (0.2 M) of ethylene episulfide was introduced below the surface of the solution with stirring at room temperature. A strongly exothermic reaction occurred. The temperature of the mixture rose rapidly to 70° C. About one-half of the episulfide was lost due to evaporation. Most of the remainder reacted with the thiol to form a liquid product. Some solid byproduct, thought to be polyethylene sulfide, was also formed. The mixture was filtered and the filtrate was further reacted with 9 g. (0.13 M) of additional episulfide. This second addition of episulfide was made dropwise to a stirred ice-cooled reaction mixture at a temperature below 22° C.

The general reaction may be described by the following equation:

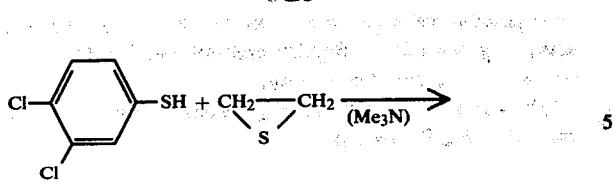

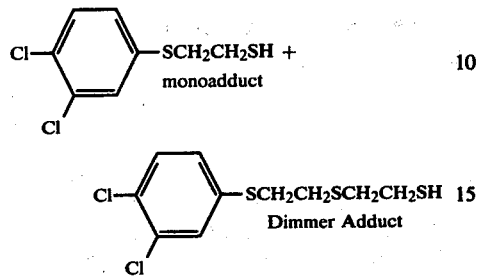

After several days standing at room temperature, the crude reaction product was fractionated by distillation in vacuo. The first fraction distilled at 98°–100° C. at 0.1 mm as a colorless liquid. It was the monoadduct. Its quantity, 21.5 g., corresponds to a yield of 45%. Some of the diadduct, 4 g., was distilled at 140° C. at 0.1 mm, also as a colorless liquid. However, nmr showed that the residue, 24 g., was also mostly the diadduct. On this basis the total yield of the diadduct was 47%.

Analyses calculated for monoadduct, $C_8H_8Cl_2S_2$: C, 40.17; H, 3.37; S, 26.81. Found: C, 40.13; H, 3.67; S, 27.25. Calculated for the diadduct $C_{10}H_{12}Cl_2S_3$: C, 40.13; H, 4.04; S, 32.14. Found: C, 40.40; H, 4.00; S, 31.65.

EXAMPLE 9

To 8.8 g. (0.1 M) isobutylene episulfide, 4.8 g. (0.1 M) methanethiol and then 0.59 g. (0.01 m) trimethylamine was condensed. The closed reaction mixture was then stirred for 72 hours at 18°. Subsequent nmr analysis of a sample indicated 14% reaction according to the following reaction scheme.

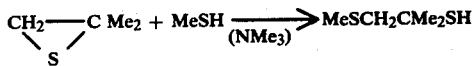

The 1-methylthio-2-methyl-2-propanethiol was isolated by fractional distillation in vacuo as a liquid boiling at 75°–76° at 25 mm pressure.

EXAMPLE 10

Triacontene episulfide is reacted with octadecylnaphthalenethiol in the presence of triethylenediamine to provide 1-octadecylnaphthylthio-2-triacontanethiol as the major product.

EXAMPLE 11

Chloropropylene episulfide is reacted with equimolar amounts of methanethiol and trimethylamine in the manner described in Example 1 to obtain the corresponding ring opening product according to the following reaction scheme.

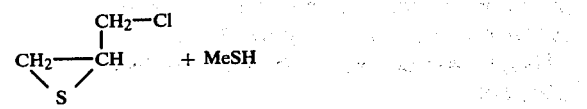

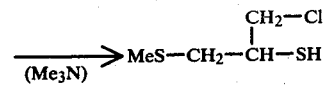

This product reacts further, however, with trimethylamine as shown below:

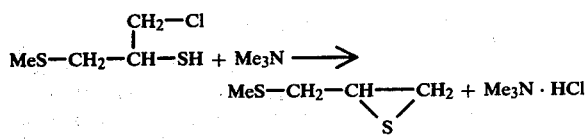

Reaction of the resulting 3-methylthio-propylene sulfide with excess methanethiol in the presence of trimethylamine under similar conditions provides 1,3-bis-methylthiopropanethiol as the major product.

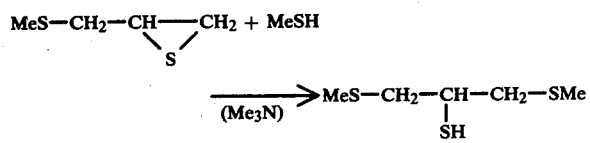

Reactions of Hydrogen Sulfide with Propylene Episulfide

EXAMPLE 12

To 37 g. (0.5 M) propylene episulfide in a Pyrex pressure tube at −70°, 8.9 g. (0.26 M) hydrogen sulfide and then 2.1 g. (0.35 M) trimethylamine were condensed. The condensation of the latter resulted in the formation of a white crystalline solid, apparently trimethylammonium sulfide. The closed tube was then placed into a 18° bath and stirred there. This resulted in obtaining a yellow, homogeneous liquid reaction mixture. However, the mixture became colorless within an hour indicating the progress of the reaction.

After 4 hours, at 18° C., the crude product was fractionally distilled in vacuo to yield the products of the following reaction:

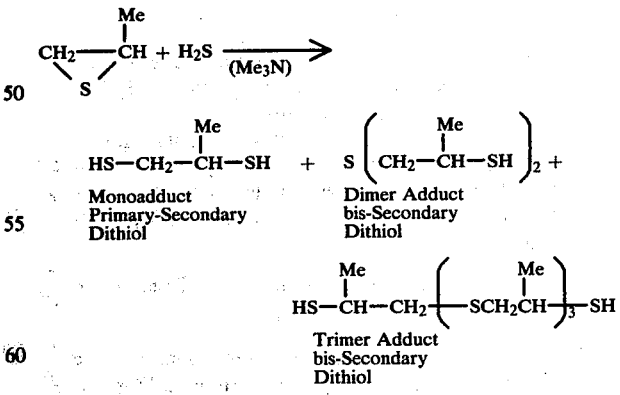

The main product of the reaction was the dimer adduct. It was obtained as 25 g. (55%) mobile liquid distillate boiling at 60°–62° at 0.05 mm. As a forerun 8.5 g. of the monoadduct, i.e. 1,2-propanedithiol, was obtained between 54°–56° at 20 mm. This amount corresponds to 15% of the theoretical yield on the basis of the episulfide used. As the last fraction, 2 g. of the trimer adduct was distilled at 97°–100° at 0.05 mm. The liquid residue, 6.5 g., was also mostly trimer adduct according to nmr analysis. Combined, they represent an about 20% yield of the trimer adduct on an episulfide basis.

The structure of the adducts was shown by nmr. Elemental analyses also supported the identity of the new compositions.

Calculated for the dimer adduct, $C_6H_{14}S_3$: C, 39.52; H, 7.73; S, 52.75. Found: C, 39.27; H, 7.65; S, 52.53.—Calculated for the trimer adduct, $C_9H_{20}S_4$: C, 42.14; H, 7.86; S, 50.00. Found: C, 41.82; H, 7.66; S, 50.29.

Polybutadiene episulfide, derived from epoxidized polybutadiene is similarly converted by excess $H_2S$ to the corresponding polythiol as indicated by the following scheme:

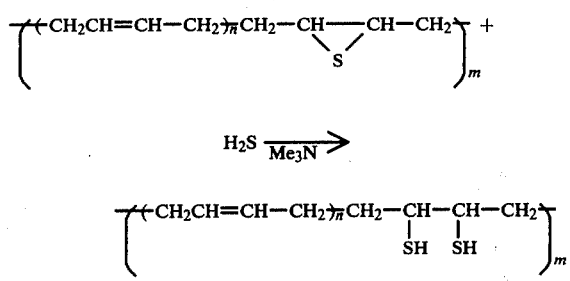

Reaction of Ethanedithiol with Propylene Episulfide

EXAMPLE 13

To a mixture of 7.4 g. (0.1 M) propylene episulfide and 4.7 g. (0.05 M) ethanedithiol, 0.1 M nitrogen base was added with stirring. The stirred mixture was then allowed to react at room temperature for 72 hours. The unreacted components were then removed by nitrogen purging at 80° under 0.1 mm pressure for one hour. The residual products were shown to originate from the following reaction:

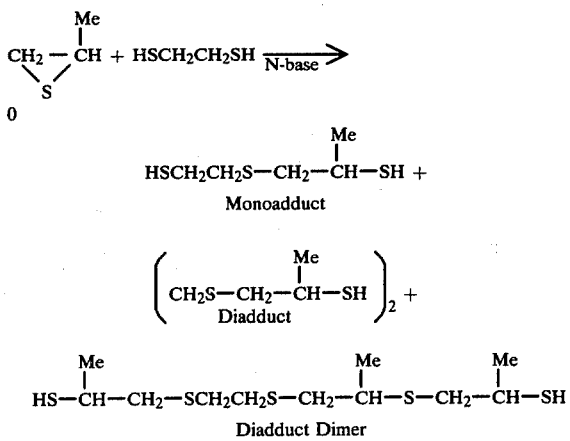

When N,N,N',N'-tetramethyl-ethylenediamine was used as the amine catalyst an exothermic reaction started on mixing. The resulting colorless liquid residual product weighed 11.4 g. This corresponds to 93% yield of the diadduct, which was shown by nmr to be the main component of the crude product.

In the case of pyridine as a catalyst no exothermicity was observed. The mixture resulting after 72 hours standing was yellow. After the removal of the volatile components, 11.3 g. of a reddish-orange liquid residual product was obtained which again consisted mainly of the diadduct.

The two crude products from the above experiments were combined and fractionally distilled in high vacuo. The distillation resulted in 4.5 g. monoadduct boiling between 55°–57° at 0.05 mm, and in 3.3 g. diadduct boiling between 97°–100° at 0.05 mm. The structure of the adducts was shown by nmr. Nmr has also indicated that the 11.6 g. residual product remaining was mostly a mixture of the diadduct and its dimer. Elemental analyses supported the assumed composition of the products.

Calculated for the monoadduct, $C_5H_{12}S_3$: C, 35.68; H, 7.18; S, 57.14. Found: C, 36.02; H, 7.12; S, 56.84.—Calculated for the diadduct, $C_8H_{18}S_4$: C, 39.63; H, 7.48; S, 52.89. Found: C, 39.45; H, 7.30; S, 53.14.

EXAMPLE 14

A mixture of 74 g. (1.0 M) propylene episulfide, 0.094 g. (0.001 M) ethanedithiol and 0.59 g. (0.01 M) trimethylamine was allowed to react in a closed tube at room temperature. The mixture became viscous with a few hours and it hardly flowed after three days. This indicated the formation of a high molecular weight polymer via the following reaction:

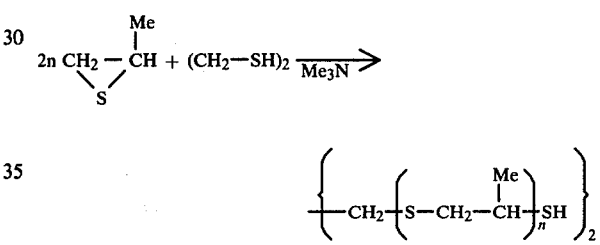

When the polymer was purged, after 7 days standing with nitrogen at 70° under 0.05 mm for 4 hours, only 1.4 g. were lost including the 0.59 g. trimethylamine. This indicated that the rest was polymerized via the above reaction to form a polymer with an average value for n equalling about 480, i.e. with an average molecular weight of 73,300.

EXAMPLE 15

To the mixture of 7.4 g. (0.1 M) propylene episulfide and 4.7 g. (0.05 M) ethanedithiol, 1.14 g. (0.1 M) bis-secondary amine catalyst, i.e. trans-2,5-dimethyl piperazine was added. After 72 hours stirring at room temperature, the yellow liquid reaction mixture was worked up by distillation. No weight loss was observed on nitrogen purging at 80° under 0.1 mm for one hour, indicating a complete reaction. However, a distillation in vacuo has indicated that, besides the reaction involving ethanedithiol, described in the previous example, a side reaction of the piperzine occurred:

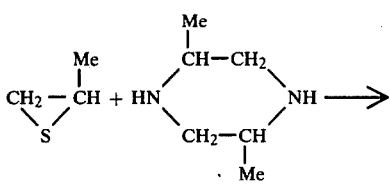

-continued

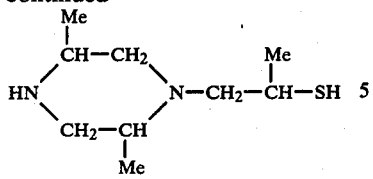

While the distillate fractions contained both the dithiol and the piperazine derived products, the residue was all derived from the dithiol. This residue was 6 g. and consisted mostly of the diadduct dimer of the previous example. As such, it represented a 60% yield based on the episulfide used.

EXAMPLE 16

A mixture of 7.4 g. (0.1 M) propylene episulfide, 4.7 g. (0.05 M) ethanedithiol and 1.2 g. (0.01 M) dimethylaniline was stirred at room temperature for 72 hours. No reaction occurred. The mixture was then heated at 100° for 24 hours. However, nmr still did not indicate any significant reaction. On purging the mixture at 80° under 0.1 mm for one hour, only 1.2 g. residue was obtained. According to nmr, this was mostly the monoadduct of Example 13.

Reaction of Trimethylene Dithiol with Propylene Episulfide

EXAMPLE 17

To a mixture of 5.4 g. (0.05 M) trimethylenedithiol and 111 g. (1.5 M) propylene episulfide placed in a dry iceacetone cooled flask, 10 g. (0.1 M) triethylamine was added. The resulting homogeneous mixture was left to stand at room temperature overnight. However, no reaction occurred; nmr examination of a sample showed the episulfide monomer to be unchanged.

To the above mixture, 5.9 g. (0.1 M) of trimethylamine was added which started an exothermic reaction. In five hours, the temperature of the mixture rose to 70° C. The mixture was then cooled to room temperature to control the reaction and allowed to stand there overnight.

Examination of the resulting viscous liquid product by nmr showed that essentially all the propylene episulfide has been polymerized. The crude polymeric product was purged with nitrogen in vacuo to remove all the volatile impurities. Removal was completed by finally heating the product at 130° C. under 0.05 mm pressure for 2 hours. The residual product, 112 g. (96% yield), was a colorless viscous oil. The reaction may be described by the following equation:

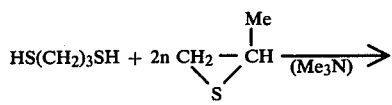

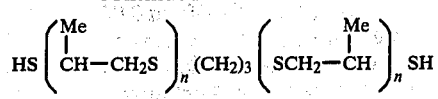

The number average molecular weight of the product was determined using a vapor pressure osmometer in benzene solution at 37° C. It was found to be 2211, indicating the presence of approximately 29 monomer units in the macromolecule. Assuming a complete conversion of the monomer, the stoichiometry of the reactants should lead to a polymer containing 30 monomer units.

The thiol functionality of the polymer was analyzed using the Zerewitinoff method for the determination of active hydrogen atoms. Calculation on the basis of the molecular weight found indicated 2.1 thiol groups per macromolecule, i.e., a thiol functionality of 2.1. The theoretical thiol functionality of the product is 2.0.

EXAMPLE 18

To a mixture of 2.7 g. (0.025 M) trimethylenedithiol and 111 g. (1.5 M) propylene episulfide, 5.9 g. (0.1 M) trimethylamine was added in dry ice-acetone. The reaction mixture was then stirred overnight in a water bath at ambient temperature. Nmr analysis of the resulting crude, viscous polymer indicated that essentially all the monomer has reacted. After the removal of the volatile components, 111 g. (97.5%) of colorless, liquid polymeric product was obtained. The molecular weight of the product was found to be 3710, requiring 49 monomer units per macromolecule. The stoichiometry of the reactants results in a monomer dithiol ratio of 60. The thiol functionality of the polymer was 2.2.

EXAMPLE 19

To a mixture of 1.62 g. (0.015 M) trimethylenedithiol and 111 g. (1.5 M) propylene episulfide, 5.9 g. (0.1 M) of trimethylamine was added slowly. The reaction mixture was polymerized as described in the previously example to yield 110 g. (98%) residual polymeric product as a colorless, viscous liquid. The molecular weight of the product was found to be 4392, indicating 59 monomer units per macromolecule.

EXAMPLE 20

To a mixture of 37 g. (0.5 M) propylene episulfide and 1.45 g. (0.0132 M) trimethylenedithiol, 2.1 g. (0.125 M) tetramethyl azabicyclooctane catalyst was added. The reaction mixture was then sealed and stirred overnight (16 hours) at room temperature. The unreacted propylene episulfide was then removed in vacuo. All volatiles were removed by heating for 2 hours at 135° C. at 0.1 mm. As a colorless liquid residue, 19 g. (50%) of oligomer was obtained. It had a molecular weight of 1405 and a thiol functionality of 2.

The reaction may be described by the following equation:

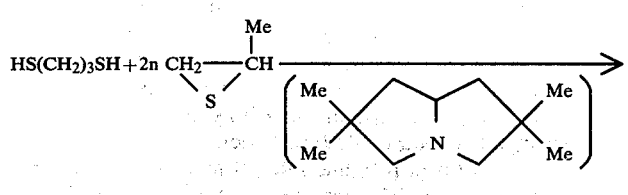

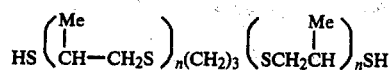

Composition calculated for $C_{57}H_{116}S_{20}$ (n=9): C, 47.39; H, 8.10; S, 44.51. Found: C, 48.46; H 8.12; S, 44.29.

EXAMPLE 21

A mixture of 37 g. (0.5 M) propylene episulfide, 1.35 g. (0.0125 M) trimethylenedithiol and 2.15 g. (0.0125 M) tetramethyl azabicyclooctane was heated with stirring in a 50° bath for 22 hours. Subsequent removal of all the volatile components resulted in 35 g. (91%) of a viscous, liquid residual product. It has a molecular weight of 2669. The calculated molecular weight for 100% monomer conversion is 3068. The thiol functionality of the oligomer was found to be 1.95.

Analyses calculated for $C_{105}H_{212}S_{36}$ (2n=34): C, 49.97; H, 8.12; S, 43.91. Found: C, 49.10; H, 8.11; S, 43.51.

EXAMPLE 22

An attempt was made to react a mixture of 3 g. (0.025 M) tetramethylenedithiol and 55.5 g. (0.75 M) propylene episulfide in the presence of 5 g. (0.05 M) triethylamine as described in the previous example. No reaction occurred on overnight standing.

The addition of 2.95 g. (0.05 M) trimethylamine to the mixture next day resulted in a slightly exothermic polymerization. The temperature of the reaction mixture rose to 40° C. during the course of 5 hours. After subsequent standing of the mixture overnight, nmr showed that at least 90% of the monomer has polymerized. After the removal of the volatile components, 47 g. (81%) of polymer was obtained as a colorless viscous liquid. This polymer had a number average molecular weight of 2181, indicating the presence of 28 monomer units in the macromolecule. The monomer-dithiol ratio was 30. Its thiol functionality was 1.9, compared with a theoretical thiol functionality of 2.0.

The reaction may be described by the following equation:

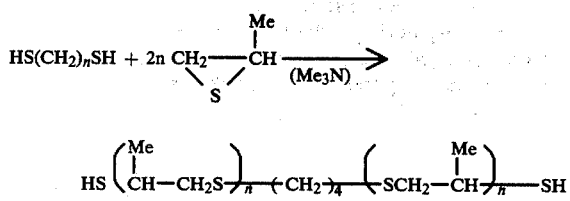

In a control experiment, a similar mixture of tetramethylenedithiol and propylene episulfide without any amine was allowed to stand at room temperature over the weekend. No reaction has occurred.

In another experiment 55.5 g. (0.75 M) propylene episulfide was polymerized with 1.5 g. tetramethylenedithiol by the addition of 2.95 g. (0.05 M) trimethylamine. The addition of the amine resulted in an exothermic reaction raising the temperature of the mixture to 62° C. Water bath cooling was therefore subsequently used overnight.

Workup of the crude reaction product the next day resulted in 56 g. (98%) residual polymer as a colorless liquid.

Examination of the resulting viscous liquid product by nmr showed that essentially all the propylene episulfide has been polymerized. The crude polymeric product was purged with nitrogen in vacuo to remove all the volatile impurities. Removal was completed by finally heating the product at 130° C. under 0.05 mm pressure for 2 hours. The residual product, 112 g. (96% yield), was a colorless viscous oil.

The number average molecular weight of the product was determined using a vapor pressure osmometer in benzene solution at 37° C. It was found to be 2211, indicating the presence of approximately 29 monomer units in the macromolecule. Assuming a complete conversion of the monomer, the stoichiometry of the reactants should lead to a polymer containing 30 monomer units.

The thiol functionality of the polymer was analyzed using the Zerewitinoff method for the determination of active hydrogen atoms. Calculation on the basis of the molecular weight found indicated 2.1 thiol groups per macromolecule, i.e., a thiol functionality of 2.1. The theoretical thiol functionality of the product is 2.0.

EXAMPLE 23

To a stirred mixture of 9.4 g. (0.1 M) ethanedithiol and 11.8 g. (0.2 M) trimethylamine, was added slowly 30 g. (0.5 M) ethylene episulfide. An exothermic reaction occurred. Although the reaction mixture was cooled with ice-water, its temperature rose to 60° C. By the time half of the episulfide was added, a colorless solid polymer precipitated from the mixture. At this point 30 ml. toluene was added to dilute the mixture. At the completion of the addition, this solid was filtered by suction, washed with methanol and dried. The resulting solid product, 30 g., was insoluble in benzene and dichlorobenzene. It is probably mostly high molecular weight polyethylenesulfide.

The reaction with the dithiol may be described by the following equation:

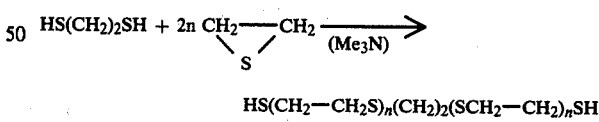

$$HS(CH_2-CH_2S)_n(CH_2)_2(SCH_2-CH_2)_nSH$$

Reaction of Dithiols with Episulfides to Form Block Copolymers

EXAMPLE 24

A block copolymer was prepared by reacting ethanedithiol with ethylene sulfide and propylene sulfide in the presence of trimethylamine. The reaction may be described by the following equation:

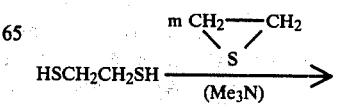

-continued

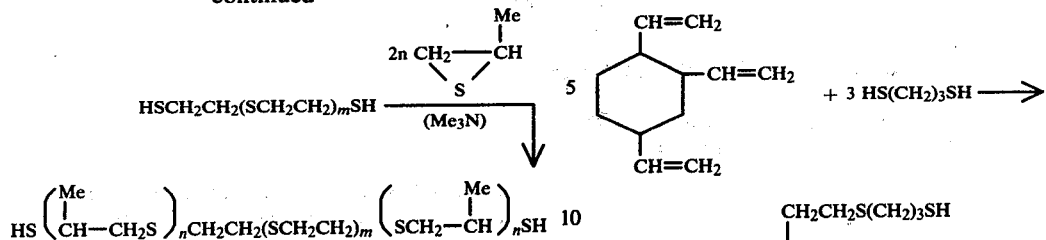

The experiment was carried out in the following manner:

To a stirred mixture of 0.94 g. (0.01 M) ethanedithiol and 1.18 g. (0.02 M) trimethylamine, an episulfide mixture consisting of 3.0 (0.05 M) ethylene episulfide and 8.88 g. (0.12 M) propylene episulfide was added in small increments. After the addition of the first 2-3 g., the temperature rose to 60° C. The mixture was cooled by dry ice-acetone. Nevertheless, subsequent additions repeatedly resulted in temperatures as high as 100° C. Nmr of a sample, taken immediately after the completion indicated that essentially all of the ethylene episulfide has reacted while more than half of the propylene episulfide was unconverted. Two hours after addition, both episulfides were essentially all converted and a colorless, viscous liquid product was formed. After the removal of the volatiles the product had a molecular weight of 1194. Assuming a complete conversion of both episulfides the stoichiometry of the copolymerization should give a calculated molecular weight of 1282.

Analyses calculated for: $HS[CH(CH_3)CH_2S]_6(CH_2CH_2)_6[CH_2CH(CH_3)S]_6H$, $C_{48}H_{98}S_{19}$: C, 44.88; H, 7.96; S, 47.43. Found: C, 45.18; H, 7.78; S, 47.32.

EXAMPLE 25

A liquid mixture of 11.64 g. (0.005 M) polythioether-dithiol from Example 17 and 9 g. (0.15 M) ethylene episulfide was allowed to react at room temperature over the weekend. A solid product resulted whose high temperature (150° C.) nmr in dichlorobenzene indicated the presence of an about equal number of propylenesulfide and ethylenesulfide polymer units. Five grams of the product was recrystallized from 160° C. o-dichlorobenzene, washed with methanol and dried 3.8 g. of purified copolymer. The nmr spectrum of this polymer was virtually identical with that of the crude product.

The product had the general formula:

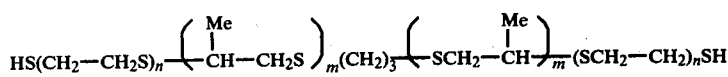

Reaction of Polythiols

EXAMPLE 26

Propylene episulfide was polymerized by reacting it with the trithiol triadduct of trimethylenedithiol and trivinyl cyclohexane in the presence of trimethylamine. The reactions involved were the following:

The trithiol triadduct of trimethylenedithiol and trivinylcyclohexane (19.3 g., 0.033 M, having a molecular weight of 580 and a thiol functionality of 2.8) was placed into a dry flask. To it were then added 74 g. (1 M) of propylene episulfide and 10 g. (0.1 m) triethylamine catalyst. The resulting homogeneous reaction mixture was allowed to stand overnight. No reaction occurred. Consequently, 5.9 g. (0.1 M) of the more powerful trimethylamine catalyst was added to effect the polymerization. Indeed, another night resulted in a viscous polymeric product, whose nmr indicated that most of the episulfide has reacted. After the removal of the volatile components 85 g. (91%) of the residual product was obtained.

The product was found to have a molecular weight of 2372. The calculated molecular weight for complete conversion is 2800. The thiol functionality of the product is 2.4. The calculated thiol functionality is 2.8.

In another experiment, a different ratio of the episulfide to trithiol was used. A mixture of 4.83 g. (0.0825 M) of the trithiol and 37 g. (0.5 M) of the episulfide was reacted in the presence of 5.9 g. (0.1 M) trimethylamine catalyst. The addition of the catalyst resulted in a mild exothermicity; a rise of the temperature to 42° C. Consequently, the reaction vessel was kept in a thermostat at room temperature overnight. Subsequent nmr analysis showed an essentially complete reaction. After the removal of the volatiles, the clear, colorless, viscous liquid product had a molecular weight of 3922. The calculated molecular weight for complete conversion is 5020. The thiol functionality of the product was found to be 2.5.

The above examples demonstrate that episulfides can be selectively reacted with thiol compounds in the presence of nitrogen bases. The resulting secondary and tertiary thioether dithiols and polythiols are useful as polymerization initiators, polymer crosslinking agents and intermediates for the preparation of chain extended and crosslinked derivatives.

The secondary thiol groups of the compositions are surprisingly suitable for crosslinking reactions with reagents known for the crosslinking of dithiols and polythiols having primary thiol groups. Due to the lower reactivity of the secondary thiols, crosslinkable compositions can be prepared having extended pot life as compared to primary thiol compositions.

Comparative Example

EXAMPLE 27

British Patent Specification No. 1,082,565 to Cameron, on page 4, under the heading "Flexibilizer C" describes reacting hydrogen sulfide and propylene sulfide in the presence of benzyldimethylamine as a catalyst at 60° C. in ethanol as a solvent. The followin experiment was conducted to show that benzyldimethylamine is not equivalent or comparable with the preferred amine catalysts of the invention, e.g., trimethylamine inasmuch as it does not rapidly catalyze the ring opening reaction at room temperature.

To a mixture of 5.4 g (0.05 M) trimethylenedithiol and 111 g. (1.5 M) propylene episulfide placed in a dry iceacetone cooled flask, 13.5 g (0.1 M) of benzyldimethylamine was added. The resulting homogeneous mixture was left to stand at room temperature (i.e., 26° C.) for 20 hours. The reaction mixture was analyzed by nmr and the nmr spectrum indicated that no reaction took place.

In contrast to the above experiment, positive results were obtained when a similar reaction was run in the presence of trimethylamine as described in Example 12, i.e., about 90% reaction took place in four (4) hours at 18° C.

These results indicate that dimethylbenzylamine is not equivalent or comparable to trimethylamine as a catalyst in the process of the invention at the lower reaction temperatures, i.e., about 40° C. and lower.

While the invention has been described in connection with specific embodiments thereof, it will be understood that it is capable of further modification and this application is intended to cover any variations, uses, or adaptions of the invention following, in general, the principles of the invention and including such departures from the present disclosure as come within known or customary practice in the art to which the invention pertains and as may be applied to the essential features hereinbefore set forth, and as fall within the scope of the invention.

What is claimed is:

1. A process for preparing a thiol terminated stereoregular polythioether compound having 3 to 20,000 recurring alkylene sulfide groups which comprises reacting at least one unsymmetrical episulfide with a sulfur compound selected from the group consisting of hydrogen sulfide, organic thiols, and mixtures thereof in the presence of a catalyst selected from the group consisting of trimethylamine, tetramethyl azabicyclooctane, N,N,N',N'-tetramethyl-ethylenediamine, trans-2,5-dimethyl piperazine, and triethylenediamine.

2. The process of claim 1 wherein the sulfur compound has the general formula $R^m(SH)_m$ wherein R is an organic radical and m is the valence of said radical.

3. The process of claim 2 wherein R is a hydrocarbyl radical or substituted hydrocarbyl radical of about $C_1$ to about $C_{30}$ carbon atoms and m is about 1 to about 10.

4. The process of claim 3 wherein R is a $C_1$ to $C_{10}$ aliphatic hydrocarbon radical and m is about 1 to 4.

5. The process of claim 1 wherein the organic thiol is a $C_1$ to $C_{30}$ hydrocarbyl dithiol or a $C_1$ to $C_{30}$ substituted hydrocarbyl dithiol.

6. The process of claim 5 wherein the organic thiol is a $C_2$ to $C_6$ alkylene dithiol.

7. The process of claim 1 wherein the organic thiol is a $C_1$ to $C_{30}$ hydrocarbyl monothiol or a $C_1$ to $C_{30}$ substituted hydrocarbyl monothiol.

8. The process of claim 1 wherein the organic thiol is a $C_1$ to $C_{30}$ hydrocarbyl monothiol or a $C_1$ to $C_{30}$ substituted hydrocarbyl trithiol.

9. The process of claim 1 wherein the episulfide has the general formula:

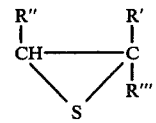

wherein R', R" and R'" are hydrogen, hydrocarbyl radicals or substituted hydrocarbyl radicals.

10. The process of claim 1 wherein the episulfide is propylene sulfide.

11. The process of claim 1 wherein at least two different episulfides are reacted with said sulfur compound.

12. The process of claim 1 wherein the catalyst is trimethylamine.

13. The process of claim 1 wherein the process is conducted at a temperature ranging from about 25° to about 40° C.

14. A process for preparing stereoregular diterminalthioether dithiol compounds having 3 to 20,000 recurring alkylene sulfide groups which comprises reacting at least one unsymmetrical episulfide with hydrogen sulfide in the presence of a catalyst selected from the group consisting of trimethylamine, tetramethyl azabicyclooctane, N,N,N',N'-tetramethyl-ethylenediamine, trans-2,5-dimethyl piperazine and triethylenediamine.

15. The process of claim 14 wherein the catalyst is trimethylamine.

16. The process of claim 14 wherein the process is conducted at a temperature ranging from about 25° to about 40° C.

17. A process for preparing secondary and tertiary thiol terminated stereoregular polythioether compounds having 3 to 20,000 recurring alkylene sulfide groups which comprises reacting a sulfur compound selected from the group consisting of hydrogen sulfide, organic thiols and mixtures thereof with at least one unsymmetrical episulfide of the formula:

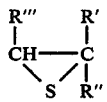

wherein R', R" and R'" are selected from the group consisting of hydrogen, hydrocarbyl radicals and substituted hydrocarbyl radicals with the proviso that R', R" and R'" are not the same and if R" is hydrogen, R'" must also be a hydrogen, wherein said reaction is conducted in the presence of a catalyst comprising trimethylamine.

18. The process of claim 17 wherein the process is conducted at a temperature ranging from about 25° to about 40° C.

19. The process of claim 17 wherein the unsymmetrical episulfide is a mono-substituted episulfide.

20. The process of claim 19 wherein R" and R'" are hydrogen and R' is a $C_1$ to $C_6$ alkyl or cycloalkyl radical.

21. A process for preparing stereoregular polythioether dithiols having 3 to 20,000 recurring alkylene sulfide groups which comprises reacting propylene sulfide with ethane dithiol in the presence of trimethylamine.

22. A secondary or tertiary polythioether thiol block copolymer having the general formula:

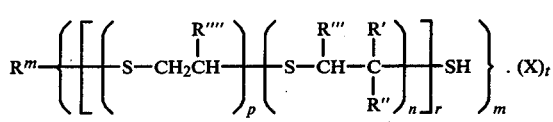

wherein R is a $C_1$ to $C_{200,000}$ hydrocarbon radical or a $C_1$ to $C_{200,000}$ hydrocarbon radical substituted with oxyethers, thioethers, esters, halogenated aromatic groups, dialkylamino groups; R' is a $C_1$ to $C_{200,000}$ hydrocarbyl or $C_1$ to $C_{200,000}$ hydrocarbyl radical substituted with hydroxy, hydrocarbyloxy, hydrocarbylthio, carbohydrocarbyloxy, acyl, alkylene sulfide and alkylene oxide groups; R" and R'" are each independently selected from the group consisting of hydrogen, $C_1$ to $C_{30}$ hydrocarbyl radicals with the proviso that if R" is hydrogen, R'" must also be hydrogen; R"" is selected from the group consisting of hydrogen and $C_1$ to $C_4$ aliphatic hydrocarbyl radical; p is an integer of 1 to about 1,000; n is an integer of 1 to about 50,000; r is an integer of 1 to about 10; m is an integer of 1 to about 500; X is a tertiary organoamine; and t is an integer of 0–10.

23. The product of claim 22 wherein R has a maximum of 1000 carbon atoms; m is an integer of about 1 to about 10; R' is a $C_1$ to $C_4$ hydrocarbon radical; R" and R'" are hydrogen; and t is an integer of 0–3.

24. The product of claim 22 wherein R is a $C_1$ to $C_{30}$ aliphatic hydrocarbon radical; R' is a $C_1$ to $C_4$ hydrocarbyl radical selected from the group consisting of alkyl, allyl, and propargyl; R', R"" are hydrogen; m is an integer of 2 or 3; p is an integer of 1 to about 1000; n is an integer of about 2 to about 3000; r is an integer of 2 to 3; and t is an integer of 0–3.

25. The product of claim 22 wherein R is a $C_2$ to $C_{12}$ hydrocarbyl radical; R' is methyl; R", R'" and R"" are hydrogen; X is trimethylamine; m is an integer of 2 or 3; n is an integer of about 1 to about 20,000; p is an integer of about 1 to about 1000 and t is an integer of 0 to 3.

26. A secondary polythioether polythiol block copolymer having the general formula:

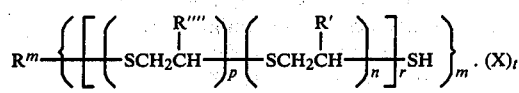

wherein R is a $C_1$ to $C_{1000}$ hydrocarbon radical, a $C_1$ to $C_{1000}$ hydrocarbon radical substituted with oxyethers, thioethers or esters; R' is selected from the group consisting of a $C_1$ to $C_{30}$ hydrocarbon radical; a $C_1$ to $C_{30}$ hydrocarbyl radical substituted with hydroxy, hydrocarbyloxy, hydrocarbylthiol, carbohydrocarbyloxy, acyl, alkylene sulfide, and alkylene oxide groups; R"" is hydrogen or $C_1$ to $C_4$ aliphatic hydrocarbyl radical; m is an integer of 1 to about 50; n is an integer of 1 to about 50,000; p is an integer of 1 to about 1,000; r is an integer of 1 to about 10; X is a tertiary organoamine; and t is an integer of 0 to 3.

27. The product of claim 26 wherein R"" is hydrogen.

28. The product of claim 26 wherein p is 1.

29. The vulcanized product of claim 26.

30. A secondary polythioether dithiol block copolymer of the formula:

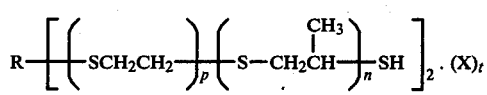

wherein R is a $C_1$ to $C_{200,000}$ divalent hydrocarbon radical or a $C_1$ to $C_{200,000}$ hydrocarbon radical substituted with oxyethers, thioethers, esters, halogenated aromatic groups, dialkylamino groups; p is an integer of 1 to about 1000; n is an integer of 1 to about 50,000; X is trimethylamine and t is an integer of 0 to 3.

31. The vulcanized product of claim 30.

32. The block copolymer of claim 30 wherein R is a divalent $C_1$–$C_{30}$ hydrocarbon radical.

33. The block copolymer of claim 30 wherein R is a divalent aliphatic hydrocarbon radical having 1 to 6 carbon atoms and t is 0.

34. The block copolymer of claim 30 wherein n is an integer of about 2 to about 3000 and t is 0.

35. A process for preparing secondary and tertiary thiol terminated stereoregular polythioether block copolymers having 3 to 20,000 recurring alkylene sulfide groups and at least two different episulfides which comprises selectively reacting said episulfides with a sulfur compound selected from the group consisting of hydrogen sulfide, organic thiols and mixtures thereof in the presence of a catalyst comprising trimethylamine.

36. The process of claim 35 wherein the reaction is carried out sequentially by first adding a first episulfide to the reaction mixture; allowing the reaction to go substantially to completion; and then adding the second episulfide to the reaction mixture.

37. The process of claim 36 wherein the episulfides are ethylene episulfide and propylene episulfide.

38. The process of claim 35 wherein the reactions are carried out at temperatures ranging from about 25° to about 40° C.

39. A polythioether thiol compound having the general formula:

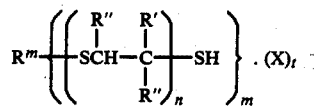

wherein R is a $C_1$ to $C_{200,000}$ hydrocarbyl radical or a $C_1$ to $C_{200,000}$ hydrocarbyl radical substituted with oxyethers, thioethers, esters, halogenated aromatic groups, and dialkylamino groups; R' is a $C_1$ to $C_{200,000}$ hydrocarbyl or $C_1$ to $C_{200,000}$ hydrocarbyl radical substituted with hydroxy, hydrocarbyloxy, hydrocarbylthio, carbohydrocarbloxy, acyl, alkylene sulfide and alkylene oxide groups; R'' and R''' are hydrogen or $C_1$ to $C_{30}$ hydrocarbyl radicals with the proviso that if R'' is hydrogen, R''' is also hydrogen; X is a tertiary organoamine n is an integer of 3 to about 1,000; m is an integer of 1 to about 10; and t is an integer of 0 to 3.

40. The thioether thiol of claim 39 wherein R has a maximum of 1000 carbon atoms; R' is a $C_1$ to $C_4$ hydrocarbyl radical; R'' and R''' are hydrogen; n is an integer of 2 to about 3,000; and m is an integer of 1 to 4.

41. The vulcanized product of claim 39.

42. The thioether thiol of claim 40 wherein m is 1.

43. The thioether thiol of claim 40 wherein m is 2.

44. The thioether thiol of claim 40 wherein m is 3.

45. Stereoregular polythioether thiol adducts having 3 to 20,000 recurring alkylene sulfide groups formed by a tertiary amine base catalyzed reaction of propylene sulfide and an organic thiol selected from the group consisting of methanethiol, ethanethiol, benzenethiol, 3,4-dichlorobenzenethiol, 4-cyanobenzenethiol, 4-nitrobenzenethiol, 4-methylthiobenzenethiol, 3-chloropropanethiol, 3-hydroxypropanethiol, 3-cyanopropanethiol, ethanedithiol, trimethylene dithiol and tetramethylenedithiol, wherein said tertiary amine catalyst is selected from the group consisting of trimethylamine, tetramethyl azabicyclooctane, N,N,N',N',tetramethylethylenediamine, trans-2,5-dimethyl piperazine and triethylenediamine.

46. Stereoregular polythioether adducts having 3 to 20,000 recurring alkylene sulfide groups formed by the trimethylamine base catalyzed reaction of propylene sulfide and an organic thiol selected from the group consisting of methanethiol, ethanethiol, ethanedithiol, trimethylene dithiol and tetramethylenedithiol.

47. Stereoregular polythioether thiol adducts having 3 to 20,000 recurring alkylene sulfide groups formed by the trimethylamine base catalyzed reaction of propylene sulfide and an organic dithiol selected from the group consisting of ethanedithiol, trimethylenedithiol and tetramethylenedithiol.

48. The polythiol of the formula:

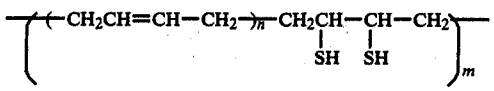

wherein m is an integer of 1 to about 50 and n is an integer from 2 to about 3000.

49. The polythioether thiol adduct of the formula:

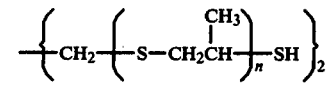

wherein n is an integer of 2 to about 3,000.

50. The polythioether thiol adduct of the formula:

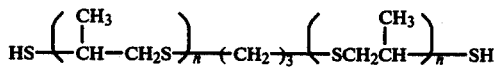

wherein n is an integer of 2 to about 3,000.

51. The polythioether thiol adduct of the formula:

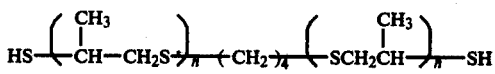

wherein n is an integer of 2 to about 3,000.

52. The polythioether thiol adduct of the formula:

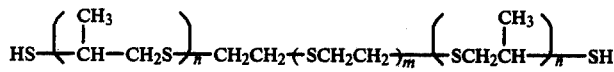

wherein m is an integer of 1 to about 50 and n is an integer of 2 to about 3,000.

53. The polythioether thiol adduct of the formula:

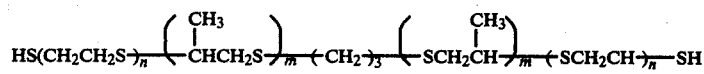

wherein m is an integer of 1 to about 50 and n is an integer of 2 to about 3,000.

54. A polythioether thiol of the formula:

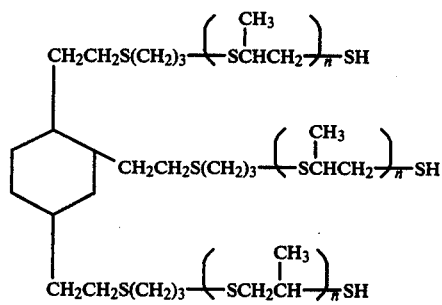

wherein n is an integer of 3 to 1000.

55. A polythioether dithiol hydrocarbyl diisocyanate polyadduct compound of the general formula:

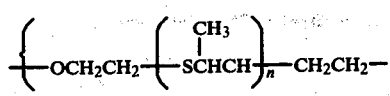
-continued
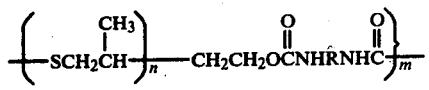
wherein n is an integer of 3 to 1000 and m is an integer of 1 to about 10, R is a $C_1$ to $C_{200,000}$ divalent hydrocarbon radical.
56. A polythioether dithiol ethylene bis-acrylate polyadduct compound of the general formula:
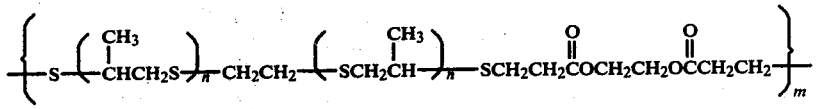
wherein n is an integer of 3 to 1000 and m is an integer of 1 to about 10.
* * * * *